United States Patent
Anzai et al.

(10) Patent No.: US 10,758,658 B2
(45) Date of Patent: *Sep. 1, 2020

(54) ARTIFICIAL LUNG AND METHOD FOR MANUFACTURING ARTIFICIAL LUNG

(71) Applicant: TERUMO KABUSHIKI KAISHA, Shibuya-ku, Tokyo (JP)

(72) Inventors: Takao Anzai, Kanagawa (JP); Takayuki Kido, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 473 days.

This patent is subject to a terminal disclaimer.

(21) Appl. No.: 15/699,381

(22) Filed: Sep. 8, 2017

(65) Prior Publication Data

US 2018/0036459 A1    Feb. 8, 2018

Related U.S. Application Data

(63) Continuation of application No. PCT/JP2016/057028, filed on Mar. 7, 2016.

(30) Foreign Application Priority Data

Mar. 10, 2015 (JP) ................................ 2015-047607
Jul. 29, 2015 (JP) ................................ 2015-150086

(51) Int. Cl.
*A61M 1/16* (2006.01)
*A61L 33/06* (2006.01)
(Continued)

(52) U.S. Cl.
CPC ......... *A61M 1/1698* (2013.01); *A61L 33/064* (2013.01); *A61M 1/1621* (2014.02);
(Continued)

(58) Field of Classification Search
CPC .. A61L 33/064; A61L 33/066; A61L 2300/42; A61L 2420/02; A61L 2207/00;
(Continued)

(56) References Cited

U.S. PATENT DOCUMENTS 4,604,412 A      8/1986 Joh et al.
6,495,101 B1 *  12/2002 Yokoyama ........... B01D 63/021
                                            128/DIG. 23
(Continued)

FOREIGN PATENT DOCUMENTS

EP    0 908 191 A1    4/1999
JP    S58-014906 A    1/1983
(Continued)

OTHER PUBLICATIONS

English Translation of the Written Opinion of the International Searching Authority (Form PCT/ISA/237) dated May 24, 2016, in corresponding International Application No. PCT/JP2016/057028. (3 pages).

(Continued)

*Primary Examiner* — Philip R Wiest
(74) *Attorney, Agent, or Firm* — Buchanan Ingersoll & Rooney PC

(57) ABSTRACT

An artificial lung is provided having a plurality of porous hollow fiber membranes for gas exchange, in which the hollow fiber membranes have outer surfaces, inner surfaces forming lumens, and opening portions through which the outer surfaces communicate with the inner surfaces, any one of the outer surfaces and the inner surfaces is coated with a colloidal solution of an antithrombotic material containing a polymer as a main component, and an average particle size of the colloid is at least 1.5 times a diameter of the opening portions of the hollow fiber membranes. An artificial lung is provided that can effectively suppress leakage of blood (Continued)

plasma components after blood circulation (blood plasma leakage).

26 Claims, 7 Drawing Sheets

(51) Int. Cl.
  *B01D 63/02* (2006.01)
  *B01D 69/08* (2006.01)
  *B01D 67/00* (2006.01)
  *B01D 71/26* (2006.01)
(52) U.S. Cl.
  CPC ....... *B01D 63/021* (2013.01); *B01D 67/0088* (2013.01); *B01D 69/08* (2013.01); *B01D 71/26* (2013.01); *A61L 2300/42* (2013.01); *A61L 2420/02* (2013.01); *A61M 2207/00* (2013.01)
(58) Field of Classification Search
  CPC .............. A61M 1/1621; A61M 1/1623; A61M 1/1625; A61M 1/1627; A61M 1/1698; B01D 67/0088; B01D 69/08; B01D 71/26
  USPC ...................................................... 422/44–48
  See application file for complete search history.

(56) References Cited

U.S. PATENT DOCUMENTS

| | | | |
|---|---|---|---|
| 2009/0206038 | A1 | 8/2009 | Thomas |
| 2014/0231333 | A1* | 8/2014 | Kelada ................. B01D 63/026 210/323.2 |

FOREIGN PATENT DOCUMENTS

| | | |
|---|---|---|
| JP | S61-004854 B2 | 2/1986 |
| JP | 11-114056 A | 4/1999 |
| JP | 3908839 B2 | 1/2007 |
| JP | 2007-295987 A | 11/2007 |
| JP | 4317183 B2 | 5/2009 |
| JP | 2009-540903 A | 11/2009 |
| JP | 2010-082067 A | 4/2010 |

OTHER PUBLICATIONS

International Search Report (PCT/ISA/210) dated May 24, 2016, by the Japanese Patent Office as the International Searching Authority for International Application No. PCT/JP2016/057028.

Office Action (Notice of Reasons for Refusal) dated Feb. 12, 2020, by the Japanese Patent Office in corresponding Japanese Patent Application No. 2017-505333 and an English Translation of the Office Action. (8 pages).

* cited by examiner

ARTIFICIAL LUNG AND METHOD FOR MANUFACTURING ARTIFICIAL LUNG

CROSS-REFERENCES TO RELATED APPLICATIONS

This application is a continuation of International Application No. PCT/JP2016/057028 filed on Mar. 7, 2016, and claims priority to Japanese Application No. 2015-047607 filed on Mar. 10, 2015 and Japanese Application No. 2015-150086 filed on Jul. 29, 2015, the entire content of all three of which is incorporated herein by reference.

TECHNICAL FIELD

The present disclosure generally relates to an artificial lung and a method for manufacturing an artificial lung. The present disclosure generally relates to a hollow fiber membrane type artificial lung for removing carbon dioxide in the blood and adding oxygen to the blood in extracorporeal blood circulation, for example, a hollow fiber membrane artificial lung of an outside blood flow type, and a method for manufacturing the same.

BACKGROUND DISCUSSION

A hollow fiber membrane type artificial lung using porous membranes generally can be used as an extracorporeal circulator or an artificial heart-lung apparatus for assisting circulation in open heart surgery for a heart disease. The hollow fiber membranes can be used for membrane type artificial lungs. Gas exchange in blood is performed through these hollow fiber membranes. As a system of blood flow to the artificial lung, there are an inside flow system in which the blood flows inside of the hollow fiber membranes and gas flows outside of the hollow fiber membranes, and an outside flow system in which, by comparison, the blood flows outside of the hollow fiber membranes and gas flows inside of the hollow fiber membranes.

In hollow fiber membrane type artificial lungs, inner surfaces or outer surfaces of the hollow fiber membranes are in contact with the blood. Therefore, there is a concern that the inner surfaces or the outer surfaces of the hollow fiber membranes in contact with the blood may affect adhesion (attachment) or activation of the platelet system. For example, an outside flow type artificial lung in which the outer surfaces of the hollow fiber membranes are in contact with the blood can generate a blood flow which can cause adhesion (attachment) or activation of the platelet system.

Considering such problems, and in view of the suppression and prevention effects of alkoxyalkyl (meth)acrylate on adhesion or activation of the platelet system, as antithrombotic material, alkoxyalkyl (meth)acrylate can be used for coating the hollow fiber membranes of an outside flow type artificial lung. For example, U.S. Pat. No. 6,495,101 B1 (corresponding to JP-A-11-114056 and EP 0 908 191 A1) discloses that outside surfaces or outer surface layers of the hollow fiber membranes are coated with a coating solution obtained by dissolving a polymer containing alkoxyalkyl (meth)acrylate as a main component in a mixed solvent of water, methanol, and ethanol, and then dried.

SUMMARY

In the hollow fiber membrane artificial lung of an outside blood flow type (e.g., manufactured by the method disclosed in U.S. Pat. No. 6,495,101 B1), adhesion or activation of the platelets can be suppressed and leakage of blood plasma components can be reduced.

For example, aiming for reducing the burden on a patient, it can be desirable to provide a technique that can further suppress the leakage of blood plasma components after blood circulation (blood plasma leakage) regardless of the flow systems.

According to one aspect, provided is an artificial lung that can effectively suppress the leakage of blood plasma components (blood plasma leakage).

As a result of intensive research to ameliorate or overcome the above problems, for example, the inventors of the present invention have found, for example, that the above problems can be ameliorate or overcome by preparing a colloidal solution of an antithrombotic material containing a polymer as a main component, and making a colloid in the solution to have an average particle size of a specific proportion or larger with respect to a diameter of opening portions (fine holes) of the hollow fiber membranes.

According to an exemplary aspect, provided is an artificial lung including a plurality of porous hollow fiber membranes for gas exchange, in which the hollow fiber membranes have outer surfaces, inner surfaces forming lumens, and opening portions through which the outer surfaces communicate with the inner surfaces. Any one of the outer surfaces and the inner surfaces is coated with a colloidal solution of an antithrombotic material containing a polymer as a main component. An average particle size of the colloid particles in the colloidal solution is at least 1.5 times a diameter of the opening portions of the hollow fiber membranes.

In addition, according to an exemplary aspect, provided is a method for manufacturing an artificial lung having a plurality of porous hollow fiber membranes for gas exchange which have outer surfaces, inner surfaces forming lumens, and opening portions through which the outer surfaces communicate with the inner surfaces. The method includes preparing a colloidal solution of an antithrombotic material containing a polymer as a main component and coating any one of the outer surfaces and the inner surfaces of the hollow fiber membranes with the colloidal solution, in which an average particle size of the colloid particles in the colloidal solution is at least 1.5 times a diameter of the opening portions of the hollow fiber membranes.

According to an exemplary aspect, provided is a method for manufacturing an artificial lung having a plurality of porous hollow fiber membranes for gas exchange which have outer surfaces, inner surfaces forming lumens, and opening portions through which the outer surfaces communicate with the inner surfaces, the method comprising: coating any one of the outer surfaces and the inner surfaces of the hollow fiber membranes with a colloidal solution of an antithrombotic material containing a polymer as a main component, wherein an average particle size of the colloid particles in the colloidal solution is at least 1.5 times a diameter of the opening portions of the hollow fiber membranes.

BRIEF DESCRIPTION OF THE DRAWINGS

In FIG. 1, disclosed are a hollow fiber membrane artificial lung of an outside blood flow type 1; a housing 2; hollow fiber membranes 3; partition walls 4 and 5; a blood inlet port 6; a blood outlet port 7; a gas inlet port 8; a gas outlet port 9; a gas inlet side header 10; a gas outlet side header 11; a blood chamber 12; a gas inlet chamber 13; and a gas outlet chamber 14, respectively.

In FIG. 2, disclosed are a hollow fiber membrane 3; an outer surface layer 3a; an outer surface 3a'; an internal layer 3b; an inner surface layer 3c; an inner surface 3c'; a passage 3d; an opening portion 3e; and an antithrombotic material 18.

In FIG. 3, disclosed are hollow fiber membranes 3; a blood chamber 17; a blood inlet portion 17a; a blood chamber 17b; a second blood chamber 17c; a hollow fiber membrane artificial lung of an outside blood flow type 20; a tubular hollow fiber membrane bundle 22; a housing 23; a gas inlet port 24; partition walls 25 and 26; a gas outlet port 27; a blood inlet port 28; blood outlet ports 29a and 29b; an inner tubular member 31; a blood circulation opening 32; an outer tubular member 33; an inner tubular body 35; an upper portion 35a of the inner tubular body 35; and a gas inlet member 41, respectively.

In FIG. 4, disclosed are hollow fiber membranes 3; a blood inlet portion 17a; a second blood chamber 17c; a tubular hollow fiber membrane bundle 22; indicate blood outlet ports 29a and 29b; an inner tubular member 31; a blood circulation opening 32; an outer tubular member 33; and an inner cylindrical body 35.

In FIG. 5, disclosed are an inner tubular member 31; and a blood circulation opening 32.

In FIG. 6, disclosed are an inner tubular member 31; and a blood circulation opening 32.

In FIG. 7, disclosed are an inner tubular member 31; and a blood circulation opening 32.

DETAILED DESCRIPTION

Figure 1:
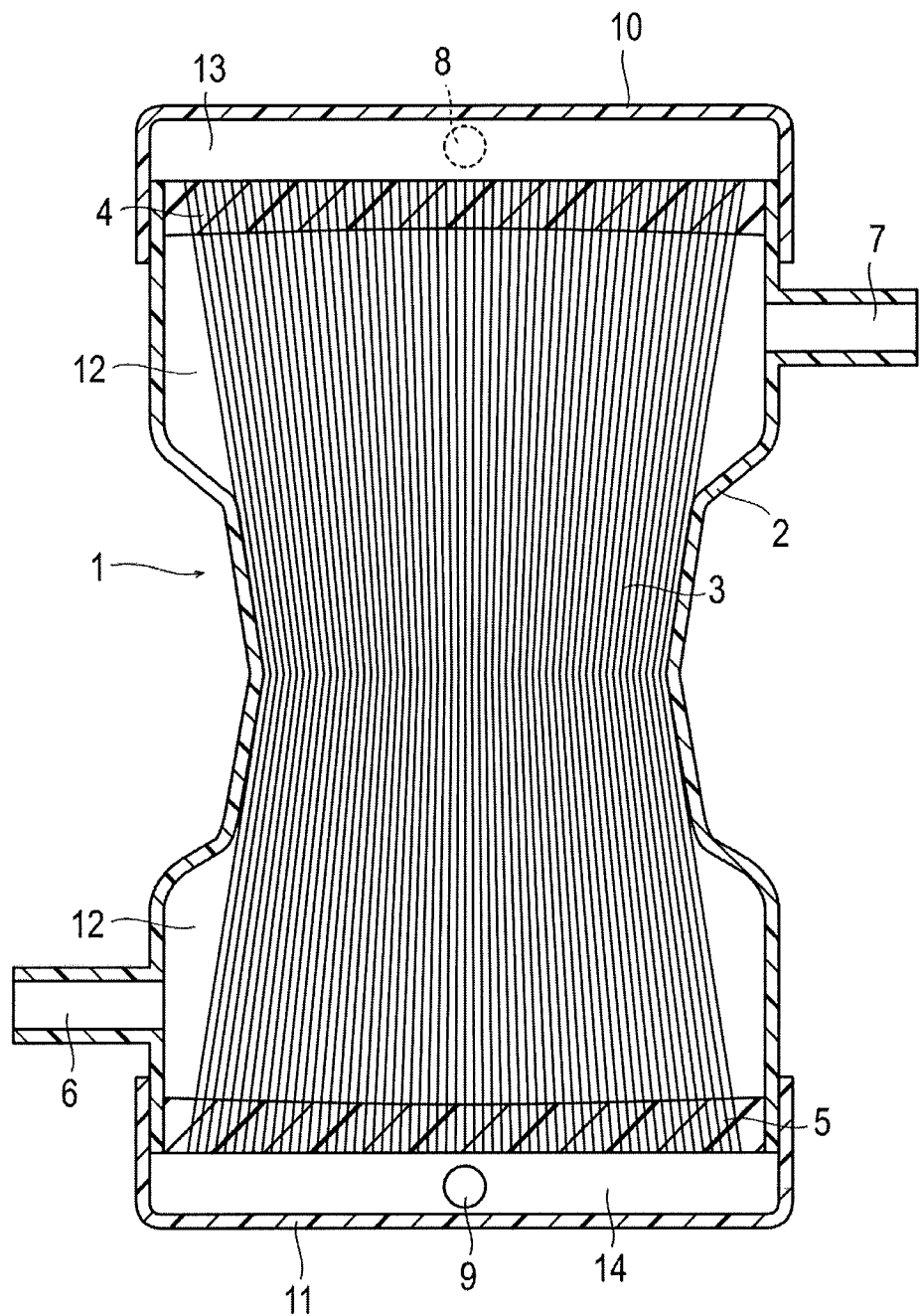
FIG. 1 is a cross-sectional view showing one embodiment of a hollow fiber membrane artificial lung of an outside blood flow type, according to one aspect.

Set forth below with reference to the accompanying drawings is a detailed description of exemplary embodiments of an artificial lung and a method for manufacturing an artificial lung.

According to one aspect, the present disclosure relates to an artificial lung having a plurality of porous hollow fiber membranes for gas exchange. The hollow fiber membranes have outer surfaces, inner surfaces forming lumens, and opening portions through which the outer surfaces communicate with the inner surfaces. Any one of the outer surfaces and the inner surfaces is coated with a colloidal solution of an antithrombotic material containing a polymer as a main component. An average particle size of the colloid particles in the colloidal solution is at least 1.5 times a diameter of the opening portions of the hollow fiber membranes. According to the exemplary artificial lung having the above configuration, the leakage of blood plasma components (blood plasma leakage) can be effectively suppressed or prevented.

In addition, the present disclosure relates to a method for manufacturing an artificial lung having a plurality of porous hollow fiber membranes for gas exchange which have outer surfaces, inner surfaces forming lumens, and opening portions through which the outer surfaces communicate with the inner surfaces. The method includes a step of preparing a colloidal solution of an antithrombotic material containing a polymer as a main component and coating any one of the outer surfaces and the inner surfaces of the hollow fiber membranes with the colloidal solution, in which an average particle size of the colloid particles in the colloidal solution in the colloidal solution is at least 1.5 times a diameter of the opening portions of the hollow fiber membranes. According to the exemplary method, it is possible to manufacture an artificial lung by which the leakage of blood plasma components (blood plasma leakage) can be effectively suppressed or prevented.

According to one aspect, an artificial lung is characterized in that a coating is provided which is formed by coating (applying) the outer surfaces or the inner surfaces of the hollow fiber membranes with a solution in which an antithrombotic material containing a polymer as a main component becomes a colloid having a certain average particle size or larger and then the colloid is dispersed. For example, the polymer can be dispersed to form colloid particles in the colloidal solution. The artificial lung using the hollow fiber membranes having the coating can effectively suppress or prevent the leakage of blood plasma components (blood plasma leakage) after circulation. A mechanism concerning the above exemplary effects of an exemplary embodiment is presumed as follows. The present invention is not limited to the following mechanism.

An artificial lung is produced by allowing a polymer-containing solution in which poly methoxyethyl acrylate (a polymer as an antithrombotic material) is dissolved in a mixed solvent of water, methanol, and ethanol (6:1:3) to flow into outer surfaces of hollow fiber membranes (blood flowing side). The entire blood contact portions of the artificial lung are then coated with a synthetic polymer. In the artificial lung produced by such a method, the leakage of blood plasma components is reduced. For example, to reduce the burden on a patient, it can be desirable that the leakage of blood plasma components from the artificial lung (hollow fiber membranes) after or during blood circulation (blood plasma leakage) is further effectively suppressed or prevented.

The inventors of the present invention have conducted intensive research, for example, to determine the reason for the blood plasma leakage (and furthermore, a deterioration in gas exchange capacity resulting from the leakage) in the hollow fiber membranes. Generally, when applying the entire blood contact portions of porous hollow fiber membranes for gas exchange with the antithrombotic material-containing solution, the antithrombotic material-containing solution penetrates into fine holes of the hollow fiber membranes (opening portions of the hollow fiber), and a small amount of the coating of the antithrombotic material is formed on an inner wall of the fine holes of the blood flowing side. Furthermore, for example, if blood circulates in such an artificial lung, the blood plasma components infiltrate into the fine holes along the coating of the antithrombotic material because of hydrophilicity of the antithrombotic material, and as a result, leakage to a side opposite to the blood flowing side occurs (i.e., blood plasma leakage occurs).

In view of the above, for example, the inventors of the present invention have considered that leakage of blood plasma components (blood plasma leakage) can be effectively suppressed or prevented, for example, by (1) suppressing formation of the coating of the antithrombotic material in the fine holes of the hollow fiber membranes as much as possible, (2) greatly reducing the amount of the antithrombotic material infiltrating into the fine holes of the hollow fiber membranes, or (3) completely preventing any infiltration of the antithrombotic material into the fine holes of the hollow fiber membranes.

Surprisingly, it has been found, for example, that leakage of blood plasma components (blood plasma leakage) can be effectively suppressed or prevented by using a colloidal solution used when applying the antithrombotic material as an application solution, and setting an average particle size of the colloid particles in the solution to be at least 1.5 times a fine hole size (diameter of the opening portions) of the hollow fiber membranes. As above, the coating of the antithrombotic material can be suppressed or prevented from being formed inside the fine holes by preparing the colloidal solution of the antithrombotic material in advance, and setting an average particle size of the colloid particles to be larger than a fine hole size of the hollow fiber membranes. As a result, for example, infiltration of the blood plasma components into the fine holes along the coat (coating) of the antithrombotic material can be suppressed or prevented. Accordingly, the artificial lung according to an exemplary aspect can effectively suppress or prevent leakage of blood plasma components (blood plasma leakage).

In For example, in the case where a membrane thickness of the hollow fiber membranes is relatively thick (i.e., there is a large difference between an outer diameter and an inner diameter), even if an antithrombotic material-containing solution penetrates into the fine holes of the hollow fiber membranes, a coating of an antithrombotic material is not completely formed on the entire inner wall of the fine holes. That is, in a case where the coating of the antithrombotic material is formed on the outer surface side, the coating of the antithrombotic material is not formed up to the inner surface side of the fine holes. Accordingly, the leakage of the blood plasma components (blood plasma leakage) into a lumen along the coating of the antithrombotic material occurs less or does not occur. On the other hand, for example, in the thin-walled hollow fiber membranes (where there is a small difference between the outer diameter and the inner diameter), because the coating of the antithrombotic material is completely formed on the entire inner wall of the fine holes easily (that is, the antithrombotic material extends to the inner surface side), the leakage of the blood plasma components into a lumen along the fine holes is likely to occur. However, even in such a case, by preparing a solution containing a colloid having a large average particle size and applying the solution in accordance with an exemplary aspect, the antithrombotic material can be suppressed from being coated into the fine holes of the hollow fiber membranes. For example, even in a case where porous membranes for gas exchange become thin or in a case where an application solution (colloidal solution) is applied in a large amount, the inner surface layers of the porous hollow fiber membranes for gas exchange can exhibit a high level of the leakage prevention effect of blood plasma. Therefore, the artificial lung according to an exemplary aspect can effectively suppress or prevent the leakage of the blood (for example, blood plasma components) even in thin-walled hollow fiber membranes. As a result, for example, it is possible to reduce the size of the hollow fiber membrane artificial lung.

Furthermore, in an exemplary artificial lung, an average particle size of the colloid particles is larger than the diameter of the fine holes of the hollow fiber membranes, and the antithrombotic material is unlikely to infiltrate into the fine holes as described above. Therefore, blocking of the fine holes of the hollow fiber membranes by the antithrombotic material itself can also be suppressed. As a result, for example, the effect of suppressing a deterioration in gas exchange capacity can be enhanced.

Hereinafter, exemplary embodiments of the present disclosure will be described. The present invention is not limited to the following embodiments. Hereinafter, the hollow fiber membrane artificial lung of an outside blood flow type will be specifically described as an exemplary embodiment. The artificial lung of the present disclosure may be the hollow fiber membrane artificial lung of an inside blood flow type, and in this case, the following embodiments can be appropriately changed to be applicable to a hollow fiber membrane artificial lung of an inside blood flow type. Furthermore, the dimensions employed in the drawings may be exaggerated for convenience of description and may differ from the actual dimensions in some cases.

In the present specification, "X to Y" indicating a range includes X and Y, and means "X or more and Y or less". In addition, unless otherwise specified, operation and measurements of physical properties or the like are measured under conditions of room temperature (20° C. to 25° C.) and at a relative humidity of 40% to 50%.

<Artificial Lung>

Hereinafter, an exemplary artificial lung of the present disclosure will be explained while referring to the drawings.

Figure 2:
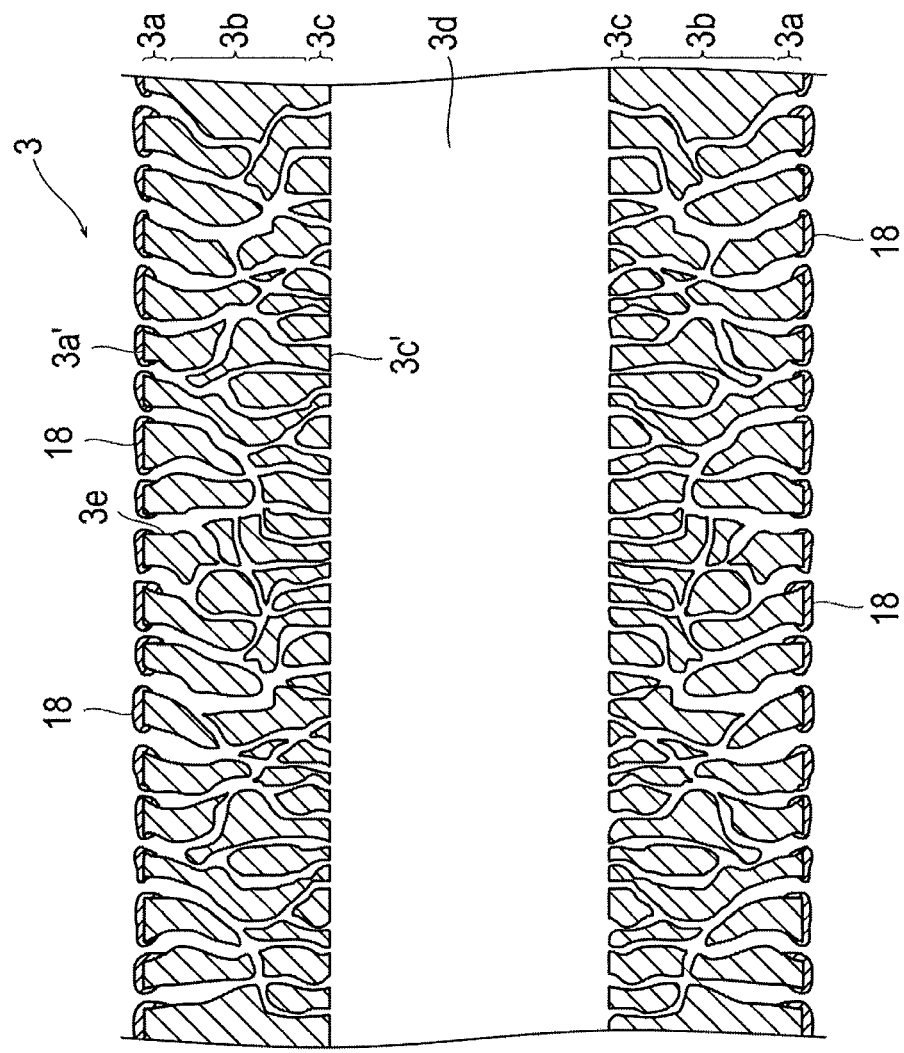
FIG. 2 is an enlarged cross-sectional view of the hollow fiber membranes used for the hollow fiber membrane artificial lung of an outside blood flow type, according to one aspect.
Figure 3:
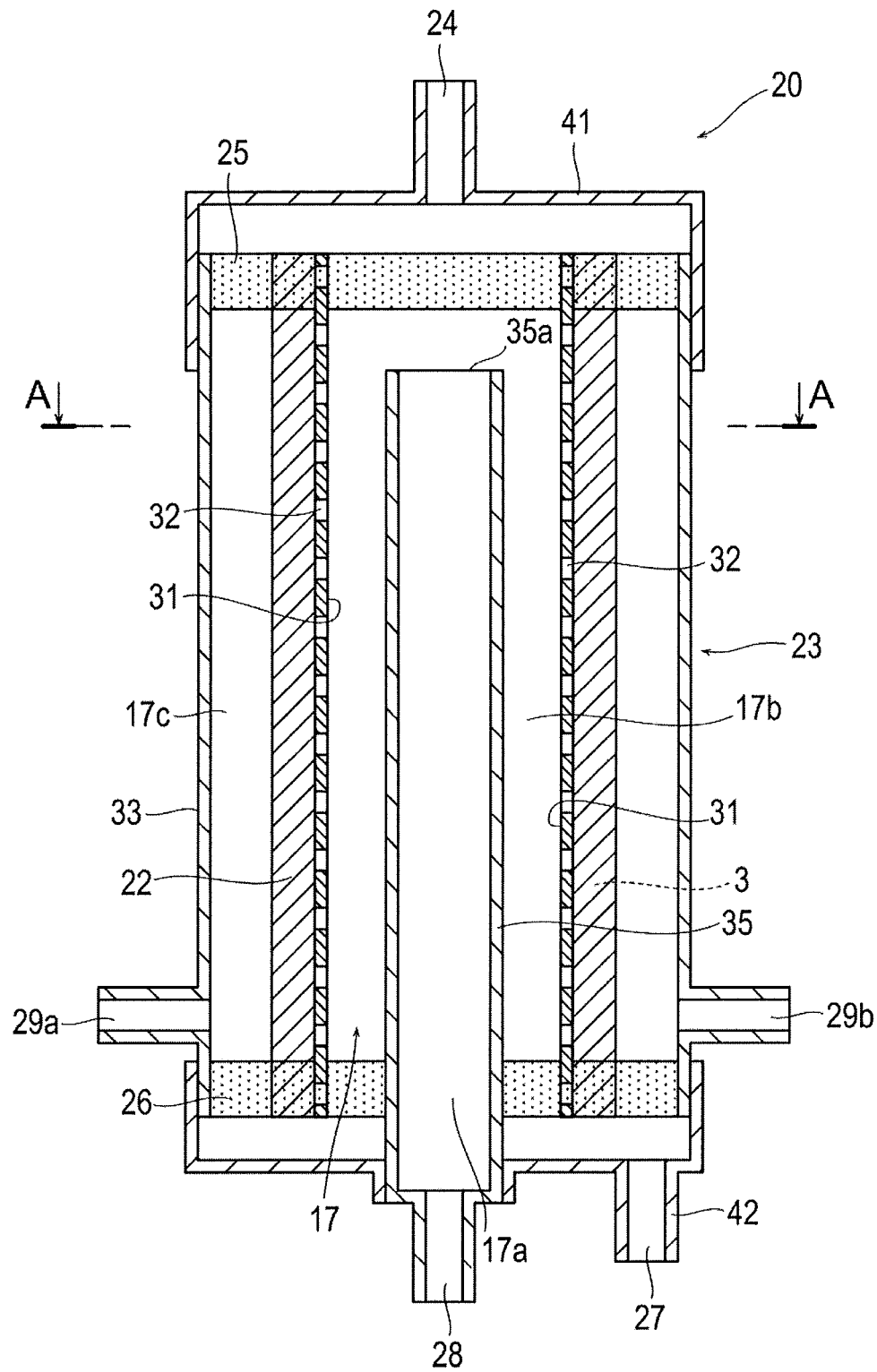
FIG. 3 is a cross-sectional view showing another embodiment of a hollow fiber membrane artificial lung of an outside blood flow type, according to one aspect.

FIG. 1 is a cross-sectional view of one embodiment of a hollow fiber membrane artificial lung of an outside blood flow type according to one aspect of the present disclosure. FIG. 2 is an enlarged cross-sectional view of the porous hollow fiber membranes for gas exchange used for the hollow fiber membrane artificial lung of an outside blood flow type according to one aspect of the present disclosure. FIG. 3 is a cross-sectional view of another embodiment of an artificial lung according to one aspect of the present disclosure.

In FIG. 1, an artificial lung 1 is an artificial lung of a type in which a large number of porous hollow fiber membranes 3 for gas exchange are accommodated in a housing 2. The blood flows into the outer side of the hollow fiber membranes 3, and an oxygen-containing gas flows to the inside of the hollow fiber membranes 3. In FIG. 2, an antithrombotic material 18 containing a polymer as a main component coats the outside surface of the hollow fiber membrane 3 which serves as the blood contact portion (outer surface 3a', or outer surface 3a' and outer surface layer 3a). A coating of the antithrombotic material 18 containing a polymer as a main component is selectively formed on the outer surfaces 3a' of the hollow fiber membranes 3. FIG. 2 shows an aspect where the coat (coating) of the antithrombotic material 18 is formed on the outer surface 3a' of the hollow fiber membrane used in the hollow fiber membrane artificial lung of an outside blood flow type. In the hollow fiber membrane of such an aspect, the outer surface 3a' side is in contact with the blood, and the oxygen-containing gas flows into an inner surface 3c' side. The present disclosure may be applied to a hollow fiber membrane artificial lung of an inside blood flow type as described above. Accordingly, the hollow fiber membrane may have a reversed configuration with respect to the above aspect, that is, an aspect in which the coating of the antithrombotic material 18 is formed on the inner surface 3c'.

In an exemplary embodiment, an antithrombotic material coats an outside surface of a hollow fiber membrane. For example, the coating of the antithrombotic material is formed on the outer surface of the hollow fiber membrane (a surface on the side where the blood flows) or on the outer surface and the outer surface layer. In an exemplary embodiment, an antithrombotic material coats an outer surface of a hollow fiber membrane. For example, the coating of the antithrombotic material is formed on the outer surface of the hollow fiber membrane (a surface on the side where the blood flows). In an exemplary embodiment, an antithrombotic material coats an outer surface layer of the hollow fiber membrane. For example, the antithrombotic material penetrates into a part of the outer surface layer of the hollow fiber membrane (for example, in the vicinity of the outer surface of the fine holes) to form the coating. In such a case, for example, no substantial antithrombotic material exists on the inside surface (inner surface) of the hollow fiber membrane (a surface on the side where the oxygen-containing gas flows) as described below in detail. That is, for example, the coating of the antithrombotic material according to one aspect of the present disclosure is selectively formed on the blood contact portion of the hollow fiber membrane (outer surface). The coating of the antithrombotic material according to one aspect of the present disclosure may be formed on at least a part of the blood contact portion of the hollow fiber membrane (outer surface), but it is exemplary that the coating is formed on the entire blood contact portion of the hollow fiber membrane (outer surface) from the viewpoint of the antithrombotic activity and biocompatibility (for example, the suppression and prevention effects of adhesion and attachment of the platelets and the suppression and prevention effects of activation of the platelets). That is, the antithrombotic material according to one aspect of the present disclosure can coat the entire blood contact portion of the artificial lung (outer surface).

In the embodiment according to FIG. 2, the antithrombotic material may exist on an internal layer 3b or an inner surface layer 3c of the hollow fiber membrane 3, but it is exemplary that no substantial material exists on the internal layer 3b or the inner surface layer 3c of the hollow fiber membrane 3. In the present specification, "no substantial antithrombotic material exists on the internal layer 3b or the inner surface layer 3c of the hollow fiber membrane 3" means that the penetration of the antithrombotic material according to one aspect of the present disclosure was not observed in the vicinity of the inside surface of the hollow fiber membrane (a surface on the side where the oxygen-containing gas flows).

A hollow fiber membrane type artificial lung 1 includes a housing 2 having a blood inlet port 6 and a blood outlet port 7, a hollow fiber membrane bundle having a large number of porous hollow fiber membranes 3 for gas exchange accommodated in the housing 2. A pair of partition walls 4 and 5 liquid-tightly support both end portions of the hollow fiber membrane bundle within the housing 2. A blood chamber 12 is formed between the inside surface of the housing 2 and the partition walls 4 and 5, and the outside surfaces of the hollow fiber membranes 3. A gas chamber is formed inside the hollow fiber membranes 3. A gas inlet port 8 and a gas outlet port 9 communicate with the gas chamber.

The hollow fiber membrane type artificial lung 1 includes the tubular housing 2, an aggregate of the hollow fiber membranes 3 for gas exchange accommodated in the tubular housing 2, and the partition walls 4 and 5 liquid-tightly retaining both end portions of the hollow fiber membranes 3 within the housing 2. The tubular housing 2 is partitioned into the blood chamber 12 that is a first fluid chamber and the gas chamber that is a second fluid chamber. The blood inlet port 6 and the blood outlet port 7 communicating with the blood chamber 12 are provided in the tubular housing 2.

A cap-like gas inlet side header 10 having the gas inlet port 8 that is a second fluid inlet port communicating with the gas chamber that is the inner spaces of the hollow fiber membranes 3, is attached above the partition walls 4 that are the end portion of the tubular housing 2. A gas inlet chamber 13 is formed of the outside surface of the partition walls 4 and the inside surface of the gas inlet side header 10. The gas inlet chamber 13 communicates with the gas chamber that is formed of the inner spaces of the hollow fiber membranes 3.

A cap-like gas outlet side header 11 having a gas outlet port 9 that is a second fluid outlet port communicating with the inner spaces of the hollow fiber membranes 3, is attached below the partition walls 5. A gas outlet chamber 14 is formed of the outside surface of the partition walls 5 and the inside surface of the gas outlet side header 11.

The hollow fiber membranes 3 are porous membranes made of a hydrophobic polymer material. Membranes suitable for use as hollow fiber membranes in an artificial lung can be used and are not particularly limited. The hollow fiber membranes (for example, the inside surfaces of the hollow fiber membranes) are made of a hydrophobic polymer material, and thus the leakage of blood plasma components can be suppressed.

An inner diameter of the hollow fiber membrane is not particularly limited, but can be 50 to 300 µm. An outer diameter of the hollow fiber membrane is not particularly limited, but can be 100 to 400 µm. The wall thickness of the hollow fiber membrane (membrane thickness) is not particularly limited, but can be 20 µm to 100 µm, for example, 25 to 100 µm, for example, 25 to 80 µm, for example, 25 to 70 µm, for example, 25 to 60 µm, for example, 25 to 50 µm, for example, 25 µm or more and less than 50 µm, for example, 25 to 45 µm, for example, 25 to 40 µm, for example, 25 to 35 µm, for example, 25 to 30 µm. In the present specification, "the wall thickness of the hollow fiber membrane" means a wall thickness between the inner surface and the outer surface of the hollow fiber membrane, and is calculated by using the expression: [(outer diameter of hollow fiber membrane)−(inner diameter of hollow fiber membrane)]/2. The wall thickness between the inner surface and the outer surface of the hollow fiber membrane can be 20 µm to 100 µm, for example, 25 to 100 µm, for example, 25 to 80 µm, for example, 25 to 70 µm, for example, 25 to 60 µm, for example, 25 to 50 µm, for example, 25 µm or more and less than 50 µm, for example, 25 to 45 µm, for example, 25 to 40 µm, for example, 25 to 35 µm, for example, 25 to 30 µm. For example, by setting a lower limit of the wall thickness of the hollow fiber membrane as above, it is possible to secure the sufficient strength of the hollow fiber membranes. Furthermore, for example, it is satisfactory in terms of labor and cost in manufacturing, and is also exemplary from the viewpoint of mass production. Furthermore, porosity of the hollow fiber membrane is not particularly limited and can be 5 to 90% by volume, for example, 10% to 80% by volume, for example, 30% to 60% by volume. A fine hole size of the hollow fiber membrane (that is, a hole size of the opening portion of the hollow fiber) is not particularly limited and can be 10 nm to 5 µm, for example, 50 nm to 1 µm, for example, 50 nm to 100 nm.

In the present specification, "a diameter of an opening portion of a hollow fiber membrane" indicates an average diameter of the opening portion on a side (for example, the outer surface side in the present embodiment) that is coated with the antithrombotic material (may simply be referred to as "fine hole," "hole size," or "fine hole size" in the present specification in some cases). Furthermore, an average diameter of the opening portion is measured by a method described below.

First, an SEM image of a side (for example, the outer surface in the present embodiment) of the hollow fiber membranes to be coated with the antithrombotic material according to one aspect of the present disclosure is captured using a scanning electron microscope (SEM). Next, the obtained SEM image is subjected to an image process, the hole portion (opening portion) is set to white, the other portions are inverted to black, and the number of pixels in the white portion is measured. A boundary level of binarization is an intermediate value of a difference between the whitest portion and the blackest portion.

Subsequently, the number of pixels of the hole displaying white (opening portion) is measured. A hole area is calculated based on the number of pixels of the hole and a resolution (μm/pixel) of the SEM image obtained as discussed above. From the obtained hole area, a diameter of each hole is calculated assuming the hole to be circular. A diameter of, for example, 500 holes is extracted, which is a statistically significant and random number, and an arithmetic average thereof is set as an average diameter of the opening portion of the hollow fiber.

As a material used for the porous membranes, for example, any suitable material used as the hollow fiber membranes in an artificial lung can be used. For example, there are a polyolefin resin such as polypropylene and polyethylene, a hydrophobic polymer material such as polysulfone, polyacrylonitrile, polytetrafluoroethylene, and cellulose acetate, and the like. Among these, a polyolefin resin is exemplary, and polypropylene is exemplary. The method for manufacturing hollow fiber membranes is not particularly limited, and any suitable method for manufacturing hollow fiber membranes can be applied or appropriately modified and applied. For example, micro fine holes can be formed on the walls of the hollow fiber membranes through a stretching method or a solid-liquid phase separation method.

As a material constituting the tubular housing 2, for example, any material suitable for use as a material used for a housing of an artificial lung can be used. For example, there is a hydrophobic synthetic resin such as polycarbonate, acrylic-styrene copolymer, and acrylic-butylene-styrene copolymer. A shape of the housing 2 is not particularly limited, and can be cylindrical and transparent, for example. The inside thereof can be easily confirmed by forming the housing to be transparent.

An accommodation amount of the hollow fiber membranes of an exemplary embodiment is not particularly limited. Any amount suitable for use in an artificial lung can be applied. For example, about 5,000 to 100,000 porous hollow fiber membranes 3 are accommodated in parallel in the housing 2 in an axial direction thereof. Furthermore, in an exemplary embodiment, both the ends of the hollow fiber membranes 3 are respectively open towards both the ends of the housing 2, and the hollow fiber membranes 3 are fixed in a liquid-tight state by the partition walls 4 and 5. The partition walls 4 and 5 are formed by a potting agent such as polyurethane and silicone rubber. A portion interposed between the above partition walls 4 and 5 in the housing 2 is divided into the gas chamber inside the hollow fiber membranes 3 and the blood chamber 12 outside the hollow fiber membranes 3.

In an exemplary embodiment, the gas inlet side header 10 having the gas inlet port 8 and the gas outlet side header 11 having the gas outlet port 9 are liquid-tightly attached to the housing 2. These headers may be formed of any material, and can be formed of a hydrophobic synthetic resin used for the housing described above, for example. The header may be attached by any method. For example, the header can be attached to the housing 2 by fusion bonding using ultrasound waves, high frequency waves, induction heating, and the like, by adhesion with an adhesive, or by mechanical engagement. In addition, the attachment may be performed by using a fastening ring (not shown). It is exemplary that the entire blood contact portion of the hollow fiber membrane type artificial lung 1 (the inside surface of the housing 2, the outside surfaces of the hollow fiber membranes 3) is formed of a hydrophobic material.

As shown in FIG. 2, the antithrombotic material 18 coats at least the outer surface 3a' (and optionally, the outer surface layer 3a) of the hollow fiber membrane 3 which serves as the blood contact portion of the hollow fiber membrane type artificial lung 1. As described above, it is exemplary that no substantial antithrombotic material exists on the internal layer 3b or the inner surface layer 3c of the hollow fiber membrane. In the case no substantial antithrombotic material exists, hydrophobic properties of the base material itself of the membrane are maintained as they are on the internal layer 3b or the inner surface layer 3c of the hollow fiber membrane, and therefore the leakage of blood plasma components can be effectively prevented. For example, it is exemplary that no substantial antithrombotic material exists on both the internal layer 3b and the inner surface layer 3c of the hollow fiber membrane. Furthermore, the hollow fiber membrane 3 includes, in the center, a passage (lumen) 3d forming the gas chamber. In addition, the hollow fiber membrane 3 includes an opening portion 3e through which the outer surface 3a' and the inner surface 3c' thereof communicate with each other. In the hollow fiber membrane having such a configuration, the blood comes into contact with outer surface 3a' coated with the antithrombotic material 18. Meanwhile, the oxygen-containing gas flows and contacts the inner surface 3c'. In one exemplary embodiment utilizing an outside flow type artificial lung, the hollow fiber membranes 3 include the inner surfaces 3c' forming the lumens where the oxygen-containing gas flows; the outer surfaces 3a' contact the blood; the outer surfaces 3a' are coated with the colloidal solution. In one exemplary embodiment utilizing an inside flow type artificial lung, the hollow fiber membranes 3 include the inner surfaces 3c' forming the lumens where the blood flows; the outer surfaces 3a' contact the flow of oxygen-containing gas; the inner surfaces 3c' are coated with the colloidal solution.

In an exemplary embodiment, the antithrombotic material coating is selectively formed on the outer surfaces of the hollow fiber membranes (outside flow type). For this reason, the blood (for example, blood plasma components) is unlikely to or does not penetrate into the inside of the fine holes of the hollow fiber membranes. Therefore, it is possible to effectively suppress or prevent blood (for example, blood plasma components) leakage from the hollow fiber membranes. For example, in a case where no substantial antithrombotic material according to one aspect of the present disclosure exists on the internal layers 3b of the hollow fiber membranes and the inner surface layers 3c of the hollow fiber membranes, the hydrophobic state of the material is maintained on the internal layers 3b of the hollow fiber membranes and the inner surface layers 3c of the hollow fiber membranes, and therefore a large amount of blood (for example, blood plasma components) leakage can be further effectively suppressed or prevented. Accordingly, in an exemplary artificial lung, a high level of gas exchange capacity can be maintained for a long period of time.

In addition, the antithrombotic material coating can be uniformly formed on the outer surfaces or the inner surfaces of the hollow fiber membranes by using the colloidal solution. For example, adhesion, attachment, and activation of the platelets are reduced on the blood contact portions of the hollow fiber membranes. Furthermore, separation of the coating from the hollow fiber membranes can be suppressed or prevented.

For example, the antithrombotic material coating is formed on the outer surfaces of the hollow fiber membranes of the artificial lung. The coating may be formed on another constituent member (for example, on the entire blood contact portion) in addition to the outer surfaces. Adhesion, attachment, and activation of the platelets can be further effectively suppressed or prevented in the entire blood contact portion of the artificial lung. In addition, since a contact angle of the blood contact surface decreases, this can facilitate a priming operation. In an exemplary embodiment, the antithrombotic material coating can be formed on the other constituent member in contact with the blood. For example, the antithrombotic material does not coat a portion other than the blood contact portions of the hollow fiber membranes, or on another portion of the hollow fiber membranes (for example, a portion buried in the partition walls). Such a portion is not in contact with the blood, and therefore, the antithrombotic material not being coated thereon does not cause a particular problem.

In addition, the artificial lung may be a type shown in FIG. 3. FIG. 3 is a cross-sectional view showing another embodiment of the artificial lung. Furthermore, FIG. 4 is a cross-sectional view taken along line A-A of FIG. 3.

In FIG. 3, an artificial lung 20 includes an inner tubular member 31 having a blood circulation opening 32 on a side surface thereof, a tubular hollow fiber membrane bundle 22 having the large number of porous hollow fiber membranes 3 for gas exchange and wound around an outside surface of the inner tubular member 31, a housing 23 accommodating the tubular hollow fiber membrane bundle 22 together with the inner tubular member 31, partition walls 25 and 26 fixing both end portions of the tubular hollow fiber membrane bundle 22 within the housing in a state where both the ends of the hollow fiber membranes 3 are open, a blood inlet port 28 and blood outlet ports 29a and 29b communicating with a blood chamber 17 formed in the housing 23, and a gas inlet port 24 and a gas outlet port 27 communicating with the insides of the hollow fiber membranes 3.

Figure 4:
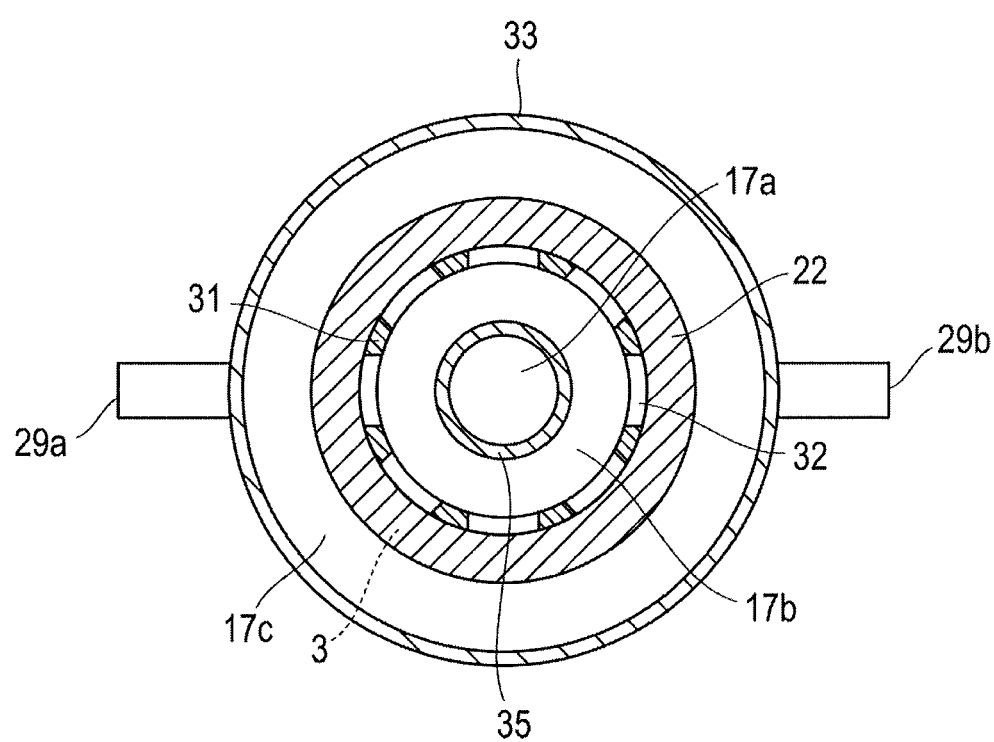
FIG. 4 is a cross-sectional view taken along line A-A of FIG. 3, according to one aspect.

In the artificial lung 20 of the present embodiment, as shown in FIG. 3 and FIG. 4, the housing 23 has an outer tubular member 33 accommodating the inner tubular member 31, the tubular hollow fiber membrane bundle 22 is accommodated between the inner tubular member 31 and the outer tubular member 33. The housing 23 has one of the blood inlet port or the blood outlet port communicating with the inside of the inner tubular member, and the other one of the blood inlet port or the blood outlet port communicating with the inside of the outer tubular member.

In the artificial lung 20 of the present embodiment, the housing 23 has an inner tubular body 35 that is accommodated in the outer tubular member 33 and the inner tubular member 31, and in which a distal end thereof is open in the inner tubular member 31. The blood inlet port 28 is formed on one end (lower end) of the inner tubular body 35, and the two blood outlet ports 29a and 29b extending outwards are formed on a side surface of the outer tubular member 33. There may be one or a plurality of the blood outlet ports.

The tubular hollow fiber membrane bundle 22 is wound around the outside surface of the inner tubular member 31. That is, the inner tubular member 31 is a core of the tubular hollow fiber membrane bundle 22. A distal end portion of the inner tubular body 35 accommodated inside the inner tubular member 31 is open in the vicinity of the first partition walls 25. In addition, the blood inlet port 28 is formed on a protruding lower end portion by the inner tubular member 31.

Each of the inner tubular body 35, the inner tubular member 31 where the hollow fiber membrane bundle 22 is wound around the outside surface thereof, and the outer tubular member 33 is arranged almost concentrically. One end (upper end) of the inner tubular member 31 where the hollow fiber membrane bundle 22 is wound around the outside surface thereof, and one end (upper end) of the outer tubular member 33 maintain the concentric positional relationship between each other by the first partition walls 25, and are in the liquid-tight state where a space formed between the inside of the inner tubular member 31, and the outer tubular member 33 and the outside surfaces of the hollow fiber membrane bundle 22 does not communicate with the outside.

Furthermore, a portion that is in a slightly upper position than the blood inlet port 28 of the inner tubular body 35, the other end (lower end) of the inner tubular member 31 where the hollow fiber membrane bundle 22 is wound around the outside surface thereof, and the other end (lower end) of the outer tubular member 33 maintain the concentric positional relationship between each other by the second partition walls 26. The above components are in a liquid-tight state where a space formed between the inside of the inner tubular member 31 and the inner tubular body 35, and a space formed between the outside surfaces of the hollow fiber membrane bundle 22 and the outer tubular member 33 do not communicate with the outside. Furthermore, the partition walls 25 and 26 are formed by a potting agent such as polyurethane and silicone rubber.

The artificial lung 20 of the present embodiment includes a blood inlet portion 17a formed by the inside of the inner tubular body 35, a first blood chamber 17b that is a substantially tubular space formed between the inner tubular body 35 and the inner tubular member 31, and a second blood chamber 17c that is a substantially tubular space formed between the hollow fiber membrane bundle 22 and the outer tubular member 33, and thereby the blood chamber 17 is formed.

The blood flowing from the blood inlet port 28 flows into the blood inlet portion 17a, moves up in the inner tubular body 35 (blood inlet portion 17a), flows out from an upper end 35a (opening end) of the inner tubular body 35, flows into the first blood chamber 17b, passes through an opening 32 formed in the inner tubular member 31, comes into contact with the hollow fiber membrane bundle 22, and after gas exchange, flows into the second blood chamber 17c, and flows out from the blood outlet ports 29a and 29b.

Furthermore, a gas inlet member 41 having the gas inlet port 24 is fixed to one end of the outer tubular member 33, and similarly, a gas outlet member 42 having the gas outlet port 27 is fixed to the other end of the outer tubular member 33. The blood inlet port 28 of the inner tubular body 35 protrudes through the gas outlet member 42.

The outer tubular member 33 is not particularly limited, and a member having a tubular body, a polygonal tube, an elliptical shape in the cross section, and the like can be used. The member can be the tubular body. Furthermore, an inner diameter of the outer tubular member is not particularly limited, and the inner diameter of the outer tubular member can be any diameter suitable for use in an artificial lung. The diameter can be approximately 32 to 164 mm. Furthermore, an effective length of the outer tubular member (that is, the portion of the length of the outer tubular member that is not buried in the partition walls) is not particularly limited, and the length can be any effective length of the outer tubular member suitable for use in an artificial lung. The effective length of the outer tubular member can be approximately 10 to 730 mm.

Furthermore, a shape of the inner tubular member 31 is not particularly limited, and for example, a member having a tubular body, a polygonal tube, an elliptical shape in a cross section, and the like can be used. The shape can be the tubular body. Furthermore, an outer diameter of the inner tubular member is not particularly limited, and the outer diameter can be any outer diameter of the inner tubular member suitable for use in an artificial lung. The outer diameter can be approximately 20 to 100 mm. Furthermore, the effective length of the inner tubular member (that is, the portion of the length of the inner tubular member that is not buried in the partition walls) is not particularly limited, and the length can be any effective length of the inner tubular member suitable for use in an artificial lung. The effective length of the inner tubular member can be approximately 10 to 730 mm.

Figure 5:
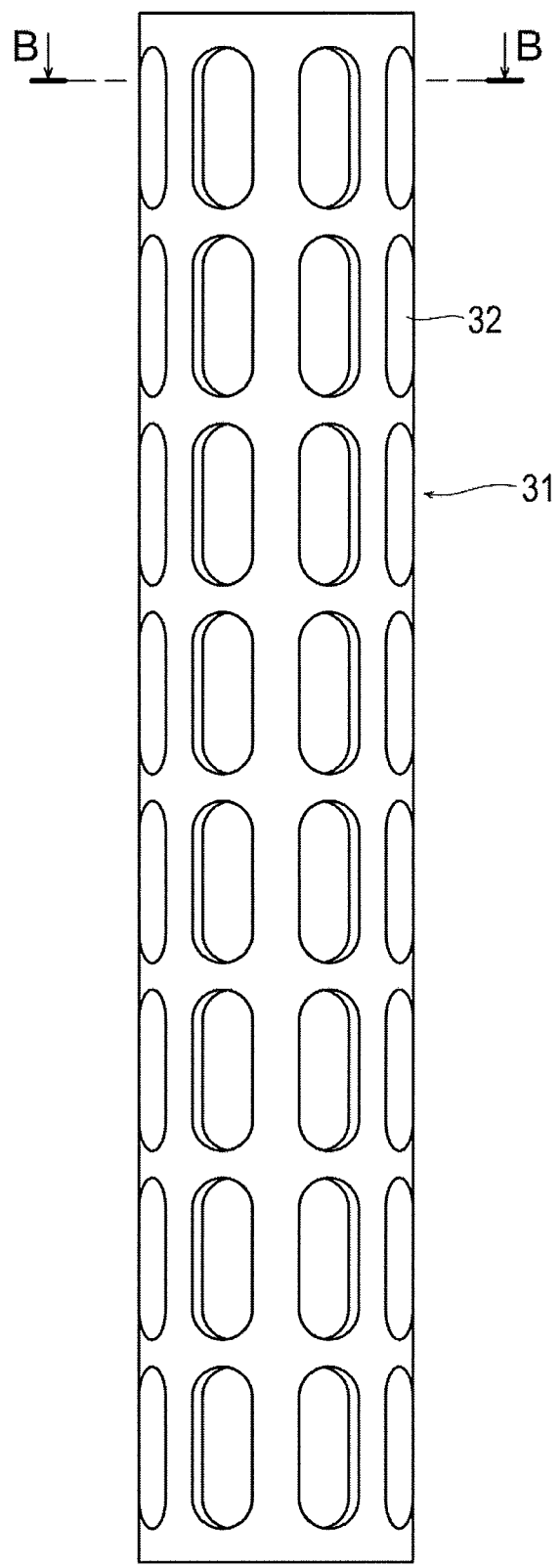
FIG. 5 is a front view showing an example of the inner tubular member used for the hollow fiber membrane artificial lung of an outside blood flow type, according to one aspect.
Figure 6:
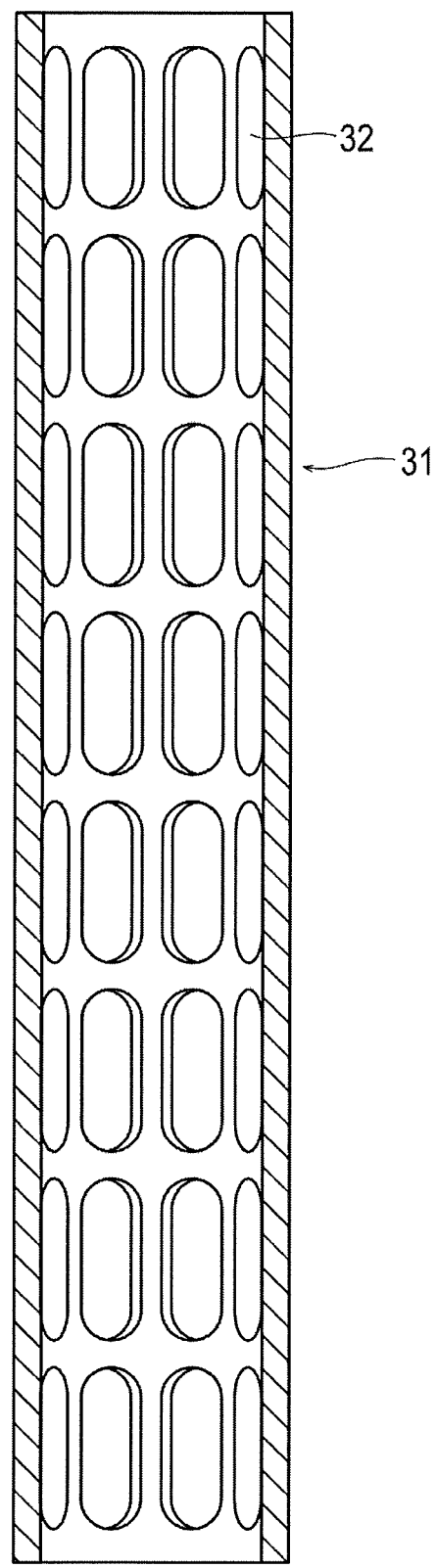
FIG. 6 is a central longitudinal cross-sectional view of the inner tubular member shown in FIG. 5, according to one aspect.
Figure 7:
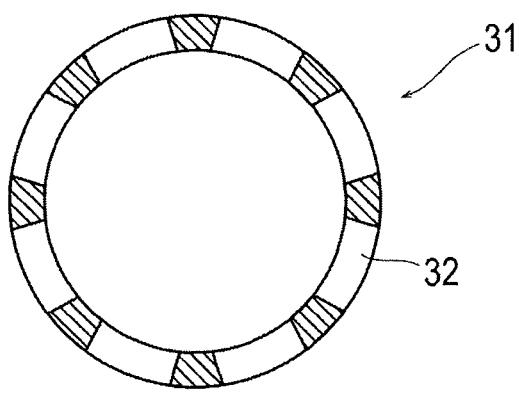
FIG. 7 is a cross-sectional view taken along line B-B of FIG. 5, according to one aspect.

The inner tubular member 31 includes a large number of blood circulation openings 32 on the side surface thereof. For example, regarding a size of the opening 32, it is exemplary that a total area is large as long as the required strength of the tubular member is maintained. As a tubular member satisfying such conditions, for example, disclosed is a tubular member having a plurality of sets of circularly arranged openings 32 in which a plurality of the openings 32 are provided on an outer peripheral surface of the inner tubular member 31. For example, the plurality of sets of circularly arranged openings can constitute 8 sets. For example, each set can include 4 to 24 openings. For example, 8 openings can be arranged in a longitudinal direction. The openings 32 can be provided at an equal angle and interval. The openings 32 can be provided in the axial direction of the tubular member at an equal interval. Exemplary blood circulation openings 32 are shown in FIG. 5 that is a front view, FIG. 6 that is a central longitudinal cross-sectional view of FIG. 5, and FIG. 7 that is a cross-sectional view taken along line B-B of FIG. 5. Furthermore, an opening shape may be a circle, a polygon, an ellipse, and the like, but an oval shape can be favorable as shown in FIG. 5.

In addition, a shape of the inner tubular body 35 is not particularly limited, and for example, a body having a tubular body, a polygonal tube, an elliptical shape in the cross section, and the like can be used. The inner tubular body can be a tubular body. Furthermore, a distance between a distal end opening of the inner tubular body 35 and the first partition walls 25 is not particularly limited, and any distance suitable for use in an artificial lung can be applied. The distance can be approximately 20 to 50 mm. Furthermore, an inner diameter of the inner tubular body 35 is not particularly limited, and the inner diameter can be any inner diameter of the inner tubular body suitable for use in an artificial lung. The inner diameter of the inner tubular body can be approximately 10 to 30 mm.

A thickness of the tubular hollow fiber membrane bundle 22 is not particularly limited, and the thickness can be any thickness of the tubular hollow fiber membrane bundle suitable for use in an artificial lung. The thickness can be 5 to 35 mm, for example, 10 mm to 28 mm. Furthermore, a filling rate of the hollow fiber membranes with respect to the tubular space formed by a space between the outside surface of the tubular hollow fiber membrane bundle 22 and the inside surface is not particularly limited, and the filling rate can be any filling rate suitable for use in an artificial lung. The filling rate can be 40% to 85%, for example, 45% to 80%. Furthermore, an outer diameter of the hollow fiber membrane bundle 22 can be any outer diameter of the hollow fiber membrane bundle suitable for use in an artificial lung. The outer diameter of the hollow fiber membrane bundle can be 30 to 170 mm, for example, 70 to 130 mm. As a gas exchange membrane, the membrane described above is used.

The hollow fiber membrane bundle 22 can be formed by winding the hollow fiber membranes around the inner tubular member 31, for example, using the inner tubular member 31 as a core, forming a hollow fiber membrane bobbin, fixing both ends of the formed hollow fiber membrane bobbin by the partition walls, and then cutting both the ends of the hollow fiber membrane bobbin together with the inner tubular member 31 that is a core. The hollow fiber membranes become open on the outside surface of the partition walls by this cutting. A method for forming hollow fiber membranes is not limited to the above method, and any suitable method for forming hollow fiber membranes can be used or appropriately modified for use.

For example, it is exemplary that one or a plurality of the hollow fiber membranes are wound around the inner tubular member 31 substantially in parallel at the same time such that adjacent hollow fiber membranes have a substantially constant interval. Therefore, blood drift can be more effectively suppressed. In addition, a distance between the hollow fiber membrane and an adjacent hollow fiber membrane is not limited to the following, but the distance is can be 1/10 to 1/1 of the outer diameter of the hollow fiber membranes. Furthermore, the distance between the hollow fiber membrane and an adjacent hollow fiber membrane can be 30 to 200 μm, for example, 50 to 180 μm.

Furthermore, it is exemplary that the hollow fiber membrane bundle 22 is formed by one or a plurality (for example, 2 to 16 membranes) of the hollow fiber membranes being wound around the inner tubular member 31 at the same time such that all adjacent hollow fiber membranes have a substantially constant interval. For example, the hollow fiber membrane bundle 22 can be formed by the hollow fiber membranes being wound around the inner tubular member 31 according to movement of a rotator for rotating the inner tubular member 31 and a winder for interweaving the hollow fiber membranes under the condition in Expression (1) when winding the hollow fiber membranes around the inner tubular member.

$$\text{traverse[mm/lot]} \times n(\text{integer}) = \text{traverse amplitude} \times 2 \pm (\text{outer diameter of fiber} + \text{interval}) \times \text{the number of windings} \quad \text{Expression (1):}$$

It is possible to further reduce the formation of blood drift by setting the condition as above. The variable n in Expression (1) represents a ratio between the number of rotations of the rotator for winding and the number of reciprocations of the winder at this time, and is not particularly limited, but is generally 1 to 5, for example, 2 to 4.

The artificial lung according to another embodiment above is a type in which the blood flows from the inside of the tubular hollow fiber membrane bundle 22, and after passing through the hollow fiber membrane bundle 22, flows to the outside of the hollow fiber membrane bundle 22, and then flows out from the artificial lung 20, but the lung is not limited thereto. The artificial lung may be a type in which the blood flows from the outside of the tubular hollow fiber membrane bundle 22, and after passing through the hollow fiber membrane bundle 22, flows to the inside of the hollow fiber membrane bundle 22, and then flows out from the artificial lung 20.

Furthermore, also in the hollow fiber membrane type artificial lung 20, it is exemplary that the antithrombotic material 18 according to one aspect of the present disclosure coats at least the outer surface 3a' (and optionally, outer surface layer 3a) of the hollow fiber membrane 3 of this hollow fiber membrane type artificial lung 1, as shown in FIG. 2. Here, the antithrombotic material according to one aspect of the present disclosure may exist on the internal layer 3b or the inner surface layer 3c of the hollow fiber membrane 3, but it is exemplary that no substantial antithrombotic material according to one aspect of the present disclosure exists on the internal layer 3b or the inner surface layer 3c of the hollow fiber membrane. In addition, the hollow fiber membrane 3 includes, in the center, the passage (lumen) 3d forming the gas chamber. In addition, the hollow fiber membrane 3 includes the opening portion 3e through which the outer surface 3a' communicates with the inner surface 3c'. The dimensions of the hollow fiber membrane (inner diameter, outer diameter, wall thickness, porosity, size of fine holes, and the like) are not particularly limited, but the same aspect as described in FIG. 1 above can be adopted.

In the artificial lung 20 according to the present embodiment, the hollow fiber membranes 3 have a bobbin shape in which membranes are in contact with each other and overlapped many times. In the present embodiment, the antithrombotic material coating is selectively and uniformly formed on the outer surfaces 3a' of the hollow fiber membranes. With such a configuration, the leakage of blood (for example, blood plasma components) to the inner surface layers 3c of the hollow fiber membranes can be suppressed or prevented. That is, the leakage of blood (for example, blood plasma components) can be effectively suppressed or prevented by the antithrombotic material selectively coating the outer surfaces 3a' (and optionally, outer surface layers 3a) of the hollow fiber membranes 3, which serve as the blood contact portion. For example, in a case where no substantial antithrombotic material according to one aspect of the present disclosure exists on the internal layers 3b and the inner surface layers 3c of the hollow fiber membranes 3, the hydrophobic state of the material is maintained on the internal layers 3b and the inner surface layers 3c of the hollow fiber membranes, and therefore a large amount of blood (for example, blood plasma components) leakage can be further effectively suppressed or prevented. In the present embodiment, the blood flow path is complicated and has many narrow portions, which is excellent for the gas exchange capacity, but the adhesion, attachment, and activation of the platelets deteriorate in some cases compared to the artificial lung of an outside blood flow type which is not a bobbin type. However, as described above, since the antithrombotic material coating is uniform, the adhesion, attachment, and activation of the platelets in the blood contact portions of the hollow fiber membranes occur less. Furthermore, separation of the coating from the hollow fiber membranes (for example, a portion where coating is uneven) can be suppressed or prevented.

The antithrombotic material coating according to the present embodiment is formed on the outer surfaces of the hollow fiber membranes of the artificial lung. The coating may be formed on another constituent member (for example, on the entire blood contact portion) in addition to the outer surfaces. The adhesion, attachment, and activation of the platelets can be further effectively suppressed or prevented in the entire blood contact portions of the artificial lung. In addition, since a contact angle of the blood contact surface decreases, this can facilitate a priming operation. In an exemplary embodiment, the antithrombotic material coating according to one aspect of the present disclosure can be formed on the other constituent member in contact with the blood. For example, the antithrombotic material does not coat a portion other than the blood contact portions of the hollow fiber membranes, or on another portion of the hollow fiber membranes (for example, a portion buried in the partition walls, and a contact portion of the hollow fiber). Such a portion is not in contact with the blood, and therefore the antithrombotic material not being coated thereon does not cause a particular problem.

<Antithrombotic Material>

According to an exemplary aspect, the antithrombotic material used for coating the outer surfaces (or the inner surfaces) of the hollow fiber membranes contains the polymer as a main component as described above. The antithrombotic material containing a polymer as a "main component" means an antithrombotic material containing 90% by weight or more of a polymer with respect to a total amount of antithrombotic material. Therefore, a minute amount of impurity components to be contained during manufacturing may be contained in the antithrombotic material. From the viewpoint of sufficiently exhibiting productivity and antithrombotic activity, it can be exemplary that the antithrombotic material contains 95% by weight or more of the polymer, for example, 100% by weight. The antithrombotic material containing 90% by weight or more of the polymer, can be confirmed by analysis using NMR, GPC and the like.

A weight average molecular weight of the "polymer" is not particularly limited, and can be 80,000 or more. As described above, in an exemplary embodiment, because the outer surfaces of the hollow fiber membranes are coated with the antithrombotic material, the antithrombotic material is used in the form of the colloidal solution, and the colloid in the solution is controlled to have a specific size. For example, from the viewpoint of ease of forming the colloid having a specific size by controlling the colloid size, a weight average molecular weight of the polymer is less than 800,000, for example, more than 200,000 and less than 800,000. A weight average molecular weight of the polymer can be 210,000 to 600,000, for example, 220,000 to 500,000, for example, 230,000 to 450,000.

In an exemplary embodiment, the content of a polymer having a relatively low molecular weight in the coating can be reduced by increasing the molecular weight of the polymer, and as a result, the effects of suppressing or preventing a polymer having a relatively low molecular weight from being eluted into blood is obtained. For example, in a case where a weight average molecular weight of the polymer is within the above range, elution of the coating (for example, a polymer having a low molecular weight) into blood can be further effectively suppressed or prevented. Furthermore, it is also exemplary in terms of antithrombotic activity and biocompatibility. In a case where a weight average molecular weight of the polymer according to one aspect of the present disclosure is excessively high, for example, the polymer in the antithrombotic material-containing solution is likely to aggregate or be precipitated, and there is a possibility that it is difficult to prepare a stable antithrombotic material-containing solution. Furthermore, in the present specification, "the polymer of a low molecular weight" means a polymer having a weight average molecular weight of less than 60,000.

In the present specification, a "weight average molecular weight" is a weight in which a value measured by gel permeation chromatography (GPC) using polystyrene as a standard substance and tetrahydrofuran (THF) as a mobile phase, is adopted. Specifically, the polymer to be analyzed is dissolved in THF to prepare a solution of 10 mg/ml. Regarding the polymer solution prepared as above, GPC column LF-804 (manufactured by Shodex) is attached to a GPC system LC-20 (manufactured by Shimadzu Corporation), THF is allowed to flow as a mobile phase, and polystyrene is used as a standard substance to measure GPC of the polymer to be analyzed. After preparing a calibration curve with a standard polystyrene, a weight average molecular weight of the polymer to be analyzed is calculated based on this curve.

For example, the polymer contained in the antithrombotic material is not particularly limited and used as long as the polymer has antithrombotic activity and biocompatibility. For example, from the viewpoint of the excellent characteristics above, the polymer can have a structural unit derived from alkoxyalkyl (meth)acrylate represented by Formula (I):

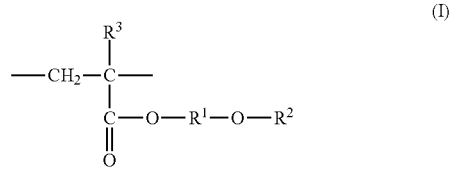

in which $R^3$ represents a hydrogen atom or a methyl group, $R^1$ represents an alkylene group having 1 to 4 carbon atoms, and $R^2$ represents an alkyl group having 1 to 4 carbon atoms.

The polymer having the structural unit represented by Formula (I) has excellent antithrombotic activity and biocompatibility (the suppression and prevention effects of the adhesion and attachment of the platelets, and the suppression and prevention effects of the activation of the platelets), for example, the suppression and prevention effects of adhesion and attachment of the platelets. For example, by using the polymer having the above structural unit, it is possible to manufacture an artificial lung that has excellent antithrombotic activity and biocompatibility (the suppression and prevention effects of the adhesion and attachment of the platelets, and the suppression and prevention effects of the activation of the platelets), for example, the suppression and prevention effects of adhesion and attachment of the platelets.

In the present specification, "(meth)acrylate" means "acrylate and/or methacrylate". That is, "alkoxyalkyl (meth)acrylate" includes all cases of only alkoxyalkyl acrylate, only alkoxyalkyl methacrylate, and alkoxyalkyl acrylate and alkoxyalkyl methacrylate.

In Formula (I), $R^1$ represents an alkylene group having 1 to 4 carbon atoms. The alkylene group having 1 to 4 carbon atoms is not particularly limited, and includes a linear or a branched alkylene group of a methylene group, an ethylene group, a trimethylene group, a tetramethylene group, and a propylene group. Among these, an ethylene group and a propylene group are exemplary, and in consideration of further enhanced effects of antithrombotic activity and biocompatibility, an ethylene group is exemplary. $R^2$ represents an alkyl group having 1 to 4 carbon atoms. The alkyl group having 1 to 4 carbon atoms is not particularly limited, and includes a linear or a branched alkyl group of a methyl group, an ethyl group, a propyl group, an isopropyl group, a butyl group, an isobutyl group, a sec-butyl group, and a tert-butyl group. Among these, a methyl group and an ethyl group are exemplary, and in consideration of further enhanced effects of antithrombotic activity and biocompatibility, a methyl group is exemplary. $R^3$ represents a hydrogen atom or a methyl group. Note that in a case where the polymer according to one aspect of the present disclosure has two or more of structural units derived from alkoxyalkyl (meth)acrylate, each structural unit may be the same or different from each other.

Specific examples of alkoxyalkyl (meth)acrylate include methoxymethyl acrylate, methoxyethyl acrylate, methoxypropyl acrylate, ethoxymethyl acrylate, ethoxyethyl acrylate, ethoxypropyl acrylate, ethoxybutyl acrylate, propoxymethyl acrylate, butoxyethyl acrylate, methoxybutyl acrylate, methoxymethyl methacrylate, methoxyethyl methacrylate, ethoxymethyl methacrylate, ethoxyethyl methacrylate, propoxymethyl methacrylate, butoxyethyl methacrylate, and the like. Among these, from the viewpoint of further enhanced effects of antithrombotic activity and biocompatibility, methoxyethyl (meth)acrylate and methoxybutyl acrylate are exemplary, and methoxyethyl acrylate (MEA) is exemplary. That is, the polymer according to one aspect of the present disclosure can be polymethoxyethyl acrylate (PMEA). The above alkoxyalkyl (meth)acrylate may be used alone or as a mixture of two or more kinds thereof.

The polymer according to one aspect of the present disclosure has a structural unit derived from alkoxyalkyl (meth)acrylate, and may be a polymer (homopolymer) having one or two or more of structural units derived from alkoxyalkyl (meth)acrylate, or may be a polymer (copolymer) having one or two or more of structural units derived from alkoxyalkyl (meth)acrylate, and one or two or more of structural units (other structural units) derived from a monomer copolymerizable with the alkoxyalkyl (meth)acrylate. In a case where the polymer according to one aspect of the present disclosure has two or more of the structural units, the structure of the polymer (copolymer) is not particularly limited, and may be any one of a random copolymer, an alternating copolymer, a periodic copolymer, or a block copolymer. In addition, the end of the polymer is not particularly limited and is appropriately determined according to the type of raw material being used, and can be a hydrogen atom.

In a case where the polymer according to one aspect of the present disclosure has structural units other than the structural units derived from alkoxyalkyl (meth)acrylate, a monomer copolymerizable with the alkoxyalkyl (meth)acrylate (copolymerizable monomer) is not particularly limited. Examples thereof include methyl acrylate, ethyl acrylate, propyl acrylate, butyl acrylate, 2-ethylhexyl acrylate, methyl methacrylate, ethyl methacrylate, propyl methacrylate, butyl methacrylate, 2-ethylhexyl methacrylate, hexyl acrylate, hexyl methacrylate, ethylene, propylene, acrylamide, N,N-dimethylacrylamide, N,N-diethylacrylamide, aminomethyl acrylate, aminoethyl acrylate, aminoisopropyl acrylate, diaminomethyl acrylate, diaminoethyl acrylate, diaminobutyl acrylate, methacrylamide, N,N-dimethylmethacrylamide, N,N-diethyl methacrylamide, aminomethyl methacrylate, aminoethyl methacrylate, diaminomethyl methacrylate, diaminoethyl methacrylate, and the like. Among these, as a copolymerizable monomer, a monomer not having a hydroxyl group or a cationic group in the molecule is exemplary. The copolymer may be any one of a random copolymer, a block copolymer, or a graft copolymer, and can be synthesized by any suitable method such as radical polymerization, ionic polymerization, and polymerization using a macromer. In all structural units of the copolymer, a ratio of the structural units derived from a copolymerizable monomer is not particularly limited, but in consideration of antithrombotic activity and biocompatibility, and the like, it is exemplary that the structural units derived from a copolymerizable monomer (the other structural units) are more than 0% by mole and 50% by mole or less with respect to all structural units of the copolymer. If the units are more than 50% by mole, there is a possibility that the effect of alkoxyalkyl (meth)acrylate deteriorates.

In addition, the polymer having a structural unit derived from alkoxyalkyl (meth)acrylate represented by Formula (I) can be produced by any suitable method.

For example, a method can be used, in which alkoxyalkyl (meth)acrylate represented by Formula (II) and one or two or more monomers (copolymerizable monomer) copolymerizable with the above alkoxyalkyl (meth)acrylate added if necessary are stirred in a polymerization solvent together with a polymerization initiator to prepare a monomer solution, and by heating the above monomer solution, alkoxyalkyl (meth)acrylate or alkoxyalkyl (meth)acrylate and a copolymerizable monomer added if necessary are (co)polymerized.

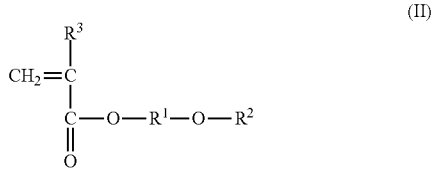

(II)

In Formula (II), substituents $R^1$, $R^2$ and $R^3$ can be the same as those defined in Formula (I).

The polymerization solvent that can be used in the above preparation of the monomer solution is not particularly limited. The solvent is capable of dissolving the alkoxyalkyl (meth)acrylate of Formula (II) and if necessary, a copolymerizable monomer. Examples thereof include water, alcohols such as methanol, ethanol, propanol, and isopropanol; aqueous solvents such as polyethylene glycols; aromatic solvents such as toluene, xylene and tetralin; halogenated solvents such as chloroform, dichloroethane, chlorobenzene, dichlorobenzene, trichlorobenzene; and the like. Among these, in consideration of alkoxyalkyl (meth)acrylate being easily dissolved and the polymer that has the above weight average molecular weight being easily obtained, methanol is exemplary.

A monomer concentration in the monomer solution is not particularly limited, but the weight average molecular weight of the polymer obtained can be increased by setting the concentration relatively high. For this reason, in consideration of the polymer that has the above weight average molecular weight being easily obtained, and the like, the monomer concentration in the monomer solution can be less than 50% by weight, for example, 15% by weight or more and less than 50% by weight. Furthermore, the monomer concentration in the monomer solution can be 20% by weight or more and 48% by weight or less, for example, 25% by weight or more and 45% by weight or less. In a case of using two or more of monomers, the above monomer concentration means a total concentration of these monomers.

The polymerization initiator is not particularly limited and any suitable initiator may be used. The initiator can be a radical polymerization initiator in terms of being excellent in polymerization stability, and examples thereof include persulfates such as potassium persulfate (KPS), sodium persulfate and ammonium persulfate; peroxides such as hydrogen peroxide, t-butyl peroxide and methyl ethyl ketone peroxide; and azo compounds such as azobisisobutyronitrile (AIBN), 2,2'-azobis(4-methoxy-2,4-dimethylvaleronitrile), 2,2'-azobis(2,4-dimethylvaleronitrile), 2,2'-azobis[2-(2-imidazolin-2-yl)propane]dihydrochloride, 2,2'-azobis[2-(2-imidazolin-2-yl)propane]disulfate dihydrate, 2,2'-azobis(2-methylpropionamidine) dihydrochloride, 2,2'-azobis[N-(2-carboxyethyl)-2-methylpropionamidine)]hydrate, 3-hydroxy-1,1-dimethylbutyl peroxyneodecanoate, α-cumyl peroxyneodecanoate, 1,1,3,3-tetrabutyl peroxyneodecanoate, t-butyl peroxyneodecanoate, t-butyl peroxyneoheptanoate, t-butyl peroxypivalate, t-amyl peroxyneodecanoate, t-amyl peroxypivalate, di(2-ethylhexyl) peroxydicarbonate, di(secondary butyl) peroxydicarbonate, and azobiscyanovaleric acid. For example, a reducing agent such as sodium sulfite, sodium hydrogen sulfite, and ascorbic acid may be used in combination with the above radical polymerization initiators as a redox type initiator. A blending amount of the polymerization initiators can be 0.0001% to 1% by mole, for example, 0.001% to 0.8% by mole, for example, 0.01% to 0.5% by mole with respect to a total amount of the monomer (alkoxyalkyl (meth)acrylate and a copolymerizable monomer added if necessary; hereinafter the same applies). Alternatively, the blending amount of the polymerization initiators can be 0.005 to 2 parts by weight, for example, 0.05 to 0.5 parts by weight with respect to 100 parts by weight of monomer (a total weight in a case of using a plurality of types of monomers). With such a blending amount of the polymerization initiators, the polymer having a desired weight average molecular weight can be more efficiently produced.

The above polymerization initiator may be mixed with the monomers and the polymerization solvent. The initiator in a solution state obtained by the initiator dissolved in another solvent in advance, may be mixed with the monomers and the polymerization solvent. In the latter case, the solvent used to dissolve the polymerization initiator is not particularly limited, as long as the polymerization initiator can be dissolved in the solvent. The solvent used to dissolve the polymerization initiator can be selected from the above polymerization solvents. Furthermore, the solvent used to dissolve the polymerization initiator may be the same as or different from the above polymerization solvent, but can be a solvent that is the same as the above polymerization solvent in consideration of the ease of control of polymerization, and the like. Furthermore, in this case, a concentration of the polymerization initiator in the solvent used to dissolve the polymerization initiator is not particularly limited, but an addition amount of the polymerization initiator can be 0.1 to 10 parts by weight, for example, 0.15 to 5 parts by weight, for example, 0.2 to 1.8 parts by weight with respect to 100 parts by weight of the solvent used to dissolve the polymerization initiator in consideration of the ease of mixing, and the like.

In a case of using the polymerization initiator in the solution state, deaeration treatment may be performed in advance before adding a solution in which the monomers are dissolved in the polymerization solvent, to the polymerization initiator solution. For the deaeration treatment, for example, an inert gas such as nitrogen gas or argon gas may be bubbled for about 0.5 to 5 hours with a methanol solution. In the deaeration treatment, the methanol solution may be adjusted to about 30° C. to 80° C., for example, to a polymerization temperature in a polymerization process described below.

Next, the above monomer solution is heated, and thus alkoxyalkyl (meth)acrylate or alkoxyalkyl (meth)acrylate and the other monomer are (co)polymerized. As a polymerization method, for example, any suitable polymerization method such as radical polymerization, anionic polymerization, and cationic polymerization can be adopted, and radical polymerization which facilitates production can be used.

Polymerization conditions are not particularly limited, as long as the above monomers (alkoxyalkyl (meth)acrylate or alkoxyalkyl (meth)acrylate and the copolymerizable monomer) can be polymerized under the conditions. For example, the polymerization temperature can be 30° C. to 60° C., for example, 40° C. to 55° C. The polymerization time can be 1 to 24 hours, for example, 3 to 12 hours. Under such conditions described above, a polymer having a high molecular weight as above can be further efficiently produced. In addition, it is possible to effectively suppress or prevent gelation in the polymerization process and to achieve high production efficiency.

In addition, a chain transfer agent, a polymerization rate-adjusting agent, a surfactant, and other additives may be appropriately used during polymerization if desired.

An atmosphere under which the polymerization reaction is carried out is not particularly limited, and the reaction may be carried out under an air atmosphere, an inert gas atmosphere such as nitrogen gas or argon gas, and the like. In addition, during the polymerization reaction, the reaction solution may be stirred.

The polymer after polymerization can be purified by a general purification method such as a reprecipitation method, a dialysis method, an ultrafiltration method, and an extraction method. For example, for the reason that a (co)polymer suitable for preparing the colloidal solution can be obtained, it is exemplary to perform purification by a reprecipitation method among the above. For example, ethanol can be used as a poor solvent used for performing reprecipitation.

The purified polymer can be dried by an arbitrary method such as freeze drying, reduced pressure drying, spray drying, and heat drying, but freeze drying or reduced pressure drying is exemplary from the viewpoint that the influence on the physical properties of the polymer is small.

<Method for Manufacturing Artificial Lung>

In the artificial lung according to one aspect, the outer surfaces or the inner surfaces of the hollow fiber membranes are coated with the above described colloidal solution containing the antithrombotic material and a solvent, an average particle size of the colloid particles in the solution is 1.5 times or larger than (i.e., at least 1.5 times) an average diameter of the opening portions of the hollow fiber membranes. Hereinafter, an exemplary aspect of a method for manufacturing the artificial lung of the present disclosure will be described. The present invention is not limited to the following exemplary aspect.

The artificial lung of one aspect of the present disclosure is manufactured by, first, preparing the colloidal solution satisfying one or more of the above characteristics, and subsequently, coating the outer surfaces or the inner surfaces of the hollow fiber membranes with the colloidal solution. An exemplary method for manufacturing an artificial lung having a plurality of porous hollow fiber membranes for gas exchange which have outer surfaces, inner surfaces forming lumens, and opening portions through which the outer surfaces communicates with the inner surfaces, includes preparing a colloidal solution of an antithrombotic material containing a polymer as a main component and applying the colloidal solution to any one of the outer surfaces and the inner surfaces of the hollow fiber membranes, in which an average particle size of the colloid particles in the colloidal solution is 1.5 times or larger than (i.e., at least 1.5 times) a diameter of the opening portions of the hollow fiber membranes. Hereinafter, (1) an exemplary step of preparing the colloidal solution and (2) an exemplary step of applying the colloidal solution coating will be explained in detail.

(1) Step of Preparing Colloidal Solution

First, the colloidal solution is prepared for coating the outer surfaces or the inner surfaces of the hollow fiber membranes. A method for manufacturing a polymer used as the antithrombotic material can be as described above.

Regarding the colloidal solution according to one aspect of the present disclosure, an average particle size of the colloid particles in the colloidal solution of the antithrombotic material contained in the solution is 1.5 times or larger than (i.e., at least 1.5 times) an average diameter of the opening portions (fine holes) of the hollow fiber membranes. That is, in an exemplary embodiment, the colloidal solution satisfies a relationship of the expression: colloid average particle size/fine hole size of hollow fiber membranes≥1.5. That is, in an exemplary embodiment, the ratio of the colloid average particle size to the fine hole size of hollow fiber membranes is greater than or equal to 1.5:1. By satisfying a relationship of the above expression, infiltration of the colloid of the antithrombotic material into the fine holes of the hollow fiber membranes can be effectively suppressed. For example, in the fine holes of the hollow fiber membrane, infiltration of the coating of the antithrombotic material up to a surface side where an oxygen-containing gas flows can be suppressed. For example, leakage of blood plasma components (blood plasma leakage) can be effectively suppressed as described above. An upper limit of a proportion of a colloid average particle size with respect to a fine hole size of the hollow fiber membranes is not particularly limited, and can be 5.0:1 or lower. If the above ratio is too high (that is, a colloid average particle size becomes too large), there is a possibility that uniform formation of the coating is difficult when applying the coating on the hollow fiber membranes. For example, by setting the ratio to 5.0:1 or lower, this may facilitate uniformly forming the coating of the antithrombotic material. For example, from the viewpoint of performing uniform formation of the coating while suppressing infiltration of the antithrombotic material into the fine holes, the above ratio (colloid average particle size/fine hole size of hollow fiber membranes), for example, can be 1.5:1 to 5.0:1, for example, 2:1 to 4:1.

An average particle size of the colloid particles in the colloidal solution depends, for example, on an average diameter of the opening portions (fine holes) of the hollow fiber membranes. In an exemplary embodiment, the average particle size is any suitable size so long as the average particle size and average diameter of the opening portions satisfy the above exemplary expression. In consideration of a practical fine hole size considering gas exchange capacity of the hollow fiber membranes used for the artificial lung, for example, an average particle size of the colloid particles in the colloidal solution can be 140 nm or larger. With such a size, for example, blocking of practical fine holes of the hollow fiber membranes by the antithrombotic material itself can be effectively suppressed. For example, it is possible to suppress not only blood plasma leakage but also a deterioration in gas exchange capacity caused by blocking of the fine holes by the antithrombotic material itself. From this viewpoint, an average particle size of the colloid particles in the colloidal solution can be 150 nm or larger. Meanwhile, an upper limit thereof is not particularly limited, but an average particle size of the colloid particles in the colloidal solution can be 400 nm or smaller. If a size is 400 nm or smaller, for example, it can become easy to uniformly coat the outer surfaces or the inner surfaces of the hollow fiber membranes with the antithrombotic material.

In the present specification, the average particle size of the colloid particles in the colloidal solution is measured by using a dynamic scattering method. Examples of a measuring device for carrying out such a dynamic scattering method include Zetasizer Nano ZS90 manufactured by Malvern Instruments Ltd. In this method, time variations of light scattering intensity by light scatterer such as fine particles are measured, the speed of Brownian motion of light scatterer is calculated from an auto-correlation function, and from this result, particle size distribution of light scatterer is calculated. In addition, measuring conditions thereof are measured by using Zetasizer Nano ZS90 manufactured by Malvern Instruments Ltd. A polymer colloid solution is put in the measurement cell, particle size measurement protocol is started, and thereby a particle size is measured.

Furthermore, it is exemplary that the colloidal solution according to the present disclosure has less fluctuation in a particle size of the colloid. For example, the colloidal solution can satisfy at least one of the following (a) and (b):

(a) a coefficient of variation (CV) of a particle size of the colloid is 30% or less, and (b) average particle size of colloid (µ)−standard deviation (σ)≥1.05×diameter of opening portions of hollow fiber membranes.

In the exemplary colloidal solution satisfying (a) and/or (b), the significant number of colloid particles in the solution is larger than a diameter of the opening portions of the hollow fiber membranes. In an exemplary embodiment, it is possible to more effectively suppress infiltration of colloid particles having a small particle size into the opening portions of the hollow fiber membranes, and thus the exemplary effect of the present disclosure can be further improved. For example, the colloidal solution used in the manufacturing method according to one aspect of the present disclosure preferably satisfies at least any one of (a) and (b).

In (a), a coefficient of variation (CV) of a particle size of the colloid is obtained by Formula (2).

Formula (2)

$$\text{Coefficient of variation}(CV) \text{ of particle size of colloid}[\%] = \frac{\text{standard deviation}(\sigma)}{\text{average particle size of colloid}(\mu)}$$

$$\frac{(\text{weight } c \text{ after immersion}(g)) - (\text{weight } a \text{ before application}(g))}{(\text{weight } b \text{ after drying the application}(g)) - (\text{weight } a \text{ before application}(g))}$$

In (a), the upper limit of CV can be, for example, 28% or less, for example, 25% or less, for example, 23% or less. Meanwhile, a lower limit of CV is not particularly limited, and can be, for example, substantially 15%.

In (b), a ratio ((µ−σ)/r) of [average particle size of colloid (µ)−standard deviation (σ)] to a diameter (r) of the opening portions of the hollow fiber membranes is preferably 1.3 or more, more preferably 1.4 or more, and particularly preferably 1.6 or more. Meanwhile, an upper limit of (µ−σ)/r is not particularly limited, and can be, for example, substantially 2.5.

A preparation method (controlling method) for the colloidal solution according to one aspect of the present disclosure is not particularly limited. For example, in an exemplary method, a relationship in which an average particle size of the colloid particles in the colloidal solution is 1.5 times or larger than (i.e., at least 1.5 times) an average diameter of the opening portions of the hollow fiber membranes is satisfied. For example, (a) a weight average molecular weight of the polymer contained in the antithrombotic material is controlled to an appropriate range; (b) a solvent is appropriately selected; (c) a concentration of the antithrombotic material in the solution is controlled to an appropriate range; (d) stirring conditions when the antithrombotic material is dispersed in the solvent are controlled to an appropriate range; and a method in which two or more of (a) to (d) are appropriately combined can be applied, for example.

Among these, exemplary details concerning (a) are described above.

Regarding (b), as a solvent used in preparation of the antithrombotic material-containing solution, it is exemplary to use a solvent that can appropriately disperse the antithrombotic material according to one aspect of the present disclosure and thereby prepare the colloidal solution. The solvent can contain water to, for example, further effectively reduce or prevent the penetration of the colloidal solution to the inner surfaces of the fine holes of the hollow fiber membranes (a surface on the side where the oxygen-containing gas flows). Water can be pure water, ion exchange water or distilled water, and among these, distilled water is exemplary. The solvent other than water, which is used in preparation of the polymer-containing solution, is not particularly limited, but can be methanol and/or acetone in consideration of dispersibility of the antithrombotic material and ease of controlling an average particle size of the colloid particles in the colloidal solution. The above solvent other than water may be used alone or in a form of a mixture of two or more kinds thereof. Among these, in consideration of dispersibility of the antithrombotic material and further ease of controlling an average particle size of the colloid particles in the colloidal solution, the solvent can be methanol. That is, the solvent can contain water and methanol. A mixing ratio of water and methanol is not particularly limited. For example, consideration of dispersibility of the antithrombotic material and further ease of controlling an average particle size of the colloid particles in the colloidal solution, the mixing ratio (volume ratio) of water:methanol can be 6:1 to 32:1, for example, 10:1 to 25:1. That is, the solvent can contain water and methanol in the mixing ratio (volume ratio) of 6:1 to 32:1, for example, can contain water and methanol in the mixing ratio (volume ratio) of 10:1 to 25:1. In a case where the solvent contains water and methanol, pH of the solvent may be adjusted to be acidic. In order to appropriately disperse the antithrombotic material according to one aspect of the present disclosure, for example, pH of the solvent (dispersion medium) can be about 5. For example, when the outer surfaces (outside flow type) or the inner surfaces (inside flow type) of the hollow fiber membranes are coated with the colloidal solution in which the antithrombotic material is dispersed in a step of colloidal solution coating (applying) to be described below, it is possible to adsorb the antithrombotic material to the artificial lung in a shorter time by adjusting the colloidal solution of the antithrombotic material according to one aspect of the present disclosure to become an acidic solution.

For example, when preparing the colloidal solution by using a mixed solvent of water and a solvent other than water, the order of adding the solvent and the antithrombotic material is not particularly limited. From the viewpoint of ease of dispersing the antithrombotic material and formation of the colloid having a uniform particle size, for example, it is exemplary to prepare the colloidal solution in the following order. For example, the antithrombotic material can be added to a solvent other than water (for example, methanol) to prepare the antithrombotic material-containing solution, and subsequently, while stirring water prepared additionally, the colloidal solution can be prepared by using the above method of adding the antithrombotic material-containing solution. An addition rate is not particularly limited, but it is exemplary to add the above antithrombotic material-containing solution to water at a rate of 5 to 100 g/min.

Regarding (c), a concentration of the polymer according to one aspect of the present disclosure in the polymer-containing solution is not particularly limited. From the viewpoint of ease of forming the coating and the effect of reducing coating unevenness, the concentration can be 0.01% to 5.0% by weight, for example, 0.05% to 1.0% by weight.

Regarding (d), it is exemplary to set stirring time and stirring temperature in preparation of the colloidal solution within an appropriate range. The stirring time after adding the antithrombotic material to the solvent is not particularly limited, but from the viewpoint of forming the colloid having a uniform particle size and ease of controlling an average particle size of the colloid particles in the colloidal solution, it is exemplary to perform stirring for 1 to 30 minutes, for example, 5 to 15 minutes. Furthermore, the stirring temperature can be 10° C. to 40° C., for example, 20° C. to 30° C.

(2) Step of Colloidal Solution Coating (Applying)

Next, for example, the outer surfaces or the inner surfaces of the hollow fiber membranes are coated with the colloidal solution of the antithrombotic material prepared in the above manner. For example, after assembling an artificial lung (for example, an artificial lung having the same structure as that of FIG. 1 or FIG. 3), the inner surfaces or the outer surfaces (that is, the blood contact portions) of the hollow fiber membranes are coated with the antithrombotic material by allowing the colloidal solution prepared in the above step (1) to come into contact therewith (or circulate). In addition, coating the hollow fiber membranes with the colloidal solution may be performed before assembling an artificial lung.

In an exemplary embodiment, the outer surfaces or the inner surfaces of the hollow fiber membranes are allowed to come into contact with the colloidal solution (for example, by circulating the colloidal solution to the blood flowing side of the artificial lung), and therefore a coated film of the polymer is formed on the outer surfaces or the inner surfaces of the hollow fiber membranes. An application amount of colloidal solution on the outer surfaces or the inner surfaces of the hollow fiber membranes is not particularly limited.

As described above, in an exemplary embodiment of the artificial lung according to one aspect of the present disclosure, an artificial lung of an outside flow type is provided in which the outer surfaces of the hollow fiber membranes are coated with the antithrombotic material. In this step, it is exemplary to coat the outer surfaces of the hollow fiber membranes with the colloidal solution in order to manufacture the artificial lung having the above configuration. For example, the manufacturing method according to one aspect of the present disclosure can be a method in which the hollow fiber membranes have the inner surfaces forming the lumens where an oxygen-containing gas flows, and the outer surfaces in contact with blood, and the outer surfaces are coated with the colloidal solution.

An antithrombotic material-coating method is not particularly limited, and any suitable method such as filling, dip coating (immersion method), spraying, spin coating, dropping, doctor blade, brush coating, roll coater, air knife coating, curtain coating, wire bar coating, gravure coating, and mixed solution-impregnated sponge coating can be applied.

A condition for forming the coated film of the antithrombotic material is not particularly limited. For example, contact time of the colloidal solution and the hollow fiber membranes (circulation time of the colloidal solution to the blood flowing side of the artificial lung) can be 1 to 5 minutes, for example, 1 to 3 minutes in consideration of the ease of forming the coated film, the effect of reducing coating unevenness, and the like. In addition, a contact temperature of the colloidal solution and the hollow fiber membranes (circulation temperature of the colloidal solution to the blood flowing side of the artificial lung) can be 5° C. to 40° C., for example, 15° C. to 30° C. in consideration of the ease of forming the coated film, the effect of reducing coating unevenness, and the like. For example, at the time of contact between the colloidal solution and the hollow fiber membranes, the colloidal solution may be allowed to stand or may be circulated. The circulation of the colloidal solution can be carried out by using any suitable method such as a roller pump.

For example, by drying the coated film after contact with the colloidal solution, the coating by the antithrombotic material according to one aspect of the present disclosure is formed on the outer surfaces or the inner surfaces of the hollow fiber membranes. A drying condition is not particularly limited. For example, the drying condition can be a condition where the coating by the antithrombotic material according to one aspect of the present disclosure, can be formed on the outer surfaces (and optionally, on the outer surface layers) or on the inner surfaces (and optionally, on inner surface layers) of the hollow fiber membranes. For example, a drying temperature can be 5° C. to 50° C., for example, 15° C. to 40° C. In addition, drying time can be 60 to 300 minutes, for example, 120 to 240 minutes. Alternatively, the coated film may be dried by allowing a gas to continuously or gradually flow into the hollow fiber membranes, the gas can be at 5° C. to 40° C., for example, at 15° C. to 30° C. The types of the gas are not particularly limited as long as, for example, a gas has no influence on the coated film and the coated film can be dried thereby. Specific examples thereof include air, an inert gas such as nitrogen gas, argon gas, and the like. A circulation amount of the gas is not particularly limited as long as, for example, it is an amount at which the coated film can be sufficiently dried, but can be 5 to 150 L, for example, 30 to 100 L.

For example, according to such an exemplary forming method, in a case where the coating is formed on the outer surface side of the hollow fiber membranes, the penetration of an antithrombotic material into the internal layers of the hollow fiber membranes and further to the inner surfaces is effectively suppressed or prevented, and therefore the antithrombotic material preferentially remains on the outer surfaces of the hollow fiber membranes. For example, in a case where the coating is formed on the inner surface side of the hollow fiber membranes, the penetration of the antithrombotic material into the internal layers of the hollow fiber membranes and further to the outer surfaces is effectively suppressed or prevented, and therefore the antithrombotic material preferentially remains on the inner surface of the hollow fiber membranes.

For example, in the artificial lung of one aspect of the present disclosure, the infiltration of blood (for example, blood plasma components) into the fine holes along the coating of the polymer occurs less or no infiltration occurs, and therefore the leakage of blood (for example, blood plasma components) can be effectively suppressed or prevented.

For example, in the artificial lung according to one aspect of the present disclosure, blood plasma leakage resistance performance can be 15 mmHg or less, for example, 10 mmHg or less, for example, 8 mmHg or less, for example, 6 mmHg or less. A lower limit of the blood plasma leakage resistance performance is not particularly limited because, for example, it can be desirable if the resistance becomes lower, and a measurement limit can be the lower limit. A method for measuring blood plasma leakage resistance performance is described below.

As describe above, the artificial lung according to one aspect of the present disclosure has a configuration in which the outer surfaces or the inner surfaces of the hollow fiber membranes are coated with the colloidal solution (the colloidal solution is applied to the outer surface or the inner surface of the hollow fiber membranes), and therefore the outer surfaces or the inner surfaces are coated with the antithrombotic material (polymer). That is, the antithrombotic material becomes a form of a coating by coating the outer surfaces or the inner surfaces of the hollow fiber membranes with the colloidal solution. For example, the configuration of an artificial lung according to one aspect can be determined by evaluating blood plasma leakage resistance performance. For example, in an exemplary embodiment, an artificial lung is provided which possesses the blood plasma leakage resistance performance described above.

EXAMPLES

Exemplary effects of the present invention will be explained using the following examples and a comparative example. But the technical scope of the present invention is not limited to the following examples. In the following examples, experiments were carried out at room temperature (25° C.) unless otherwise specified. In addition, unless otherwise specified, "%" and "part" mean "% by weight" and "parts by weight", respectively.

<Synthesis of Antithrombotic Material>

Preparation Example 1: Synthesis of PMEA Having Weight Average Molecular Weight of 250,000

15 g (0.115 mol) of 2-methoxyethyl acrylate (MEA) was dissolved in 40 g of methanol and put in a 4-neck flask, $N_2$ bubbling was carried out at 50° C. for 1 hour, and thereby a monomer solution (1) was prepared. Additionally, 0.015 g of 2,2'-azobis(4-methoxy-2,4-dimethylvaleronitrile) (V-70, manufactured by Wako Pure Chemical Industries, Ltd.) was dissolved in 5 g of methanol, and a polymerization initiator solution (1) was prepared. Next, the polymerization initiator solution (1) was added to the monomer solution (1), and the polymerization reaction was carried out at 50° C. for 5 hours. After polymerization for a predetermined time, the polymerization solution was added dropwise to ethanol, and the precipitated polymer (PMEA (1)) was recovered. When a weight average molecular weight of the recovered polymer (PMEA (1)) was measured, the weight was 250,000.

Preparation Example 2: Synthesis of PMEA Having Weight Average Molecular Weight of 310,000

60 g (0.46 mol) of 2-methoxyethyl acrylate (MEA) was dissolved in 135 g of methanol and put in a 4-neck flask, $N_2$ bubbling was carried out at 50° C. for 1 hour, and thereby a monomer solution (2) was prepared. Additionally, 0.06 g of 2,2'-azobis(4-methoxy-2,4-dimethylvaleronitrile) (V-70, manufactured by Wako Pure Chemical Industries, Ltd.) was dissolved in 5 g of methanol, and a polymerization initiator solution (2) was prepared. Next, the polymerization initiator solution (2) was added to the monomer solution (2), and the polymerization reaction was carried out at 50° C. for 5 hours. After polymerization for a predetermined time, the polymerization solution was added dropwise to ethanol, and the precipitated polymer (PMEA (2)) was recovered. When a weight average molecular weight of the recovered polymer (PMEA (2)) was measured, the weight was 310,000.

Preparation Example 3: Synthesis of PMEA Having Weight Average Molecular Weight of 420,000

80 g (0.61 mol) of 2-methoxyethyl acrylate (MEA) was dissolved in 115 g of methanol and put in a 4-neck flask, $N_2$ bubbling was carried out at 50° C. for 1 hour, and thereby a monomer solution (3) was prepared. Additionally, 0.08 g of 2,2'-azobis(4-methoxy-2,4-dimethylvaleronitrile) (V-70, manufactured by Wako Pure Chemical Industries, Ltd.) was dissolved in 5 g of methanol, and a polymerization initiator solution (3) was prepared. Next, the polymerization initiator solution (3) was added to the monomer solution (3), and the polymerization reaction was carried out at 50° C. for 5 hours. After polymerization for a predetermined time, the polymerization solution was added dropwise to ethanol, and the precipitated polymer (PMEA (3)) was recovered. When a weight average molecular weight of the recovered polymer (PMEA (3)) was measured, the weight was 420,000.

Preparation Example 4: Synthesis of PMEA Having Weight Average Molecular Weight of 800,000

100 g (0.77 mol) of 2-methoxyethyl acrylate (MEA) was dissolved in 95 g of methanol and put in a 4-neck flask, $N_2$ bubbling was carried out at 50° C. for 1 hour, and thereby a monomer solution (4) was prepared. Additionally, 0.1 g of 2,2'-azobis(4-methoxy-2,4-dimethylvaleronitrile) (V-70, manufactured by Wako Pure Chemical Industries, Ltd.) was dissolved in 5 g of methanol, and a polymerization initiator solution (4) was prepared. Next, the polymerization initiator solution (4) was added to the monomer solution (4), and the polymerization reaction was carried out at 50° C. for 5 hours. After polymerization for a predetermined time, the polymerization solution was added dropwise to ethanol, and the precipitated polymer (PMEA (4)) was recovered. When a weight average molecular weight of the recovered polymer (PMEA (4)) was measured, the weight was 800,000.

<Preparation of Coating Solution>

Example 1-1

0.4 g of PMEA (1) (weight average molecular weight=250,000) synthesized in Preparation Example 1 was dissolved in 20 g of methanol. To another container, 380 g of distilled water was added, and the methanol solution of PMEA (1) above was added at a rate of 20 g/min while stirring with a stirrer. Thereafter, the mixture was stirred at 25° C. for 10 minutes, and therefore a white turbid coating solution (1) was obtained. The coating solution (1) was a colloidal solution in which the colloid of PMEA was dispersed.

(At this time, in the solvent of the coating solution (1), a mixing ratio (volume ratio) of water:methanol=95:5, and a concentration of PMEA (1) is 0.1% by weight.)

Regarding the above coating solution (1), when a colloid average particle size was measured with Zetasizer Nano ZS90 manufactured by Malvern Instruments Ltd., an average particle size of the PMEA polymer colloid was 160 nm.

Example 1-2

A coating solution (2) was obtained in the same manner as in Example 1-1 except that PMEA used in Example 1-1 was changed to PMEA (2) (weight average molecular weight=310,000) synthesized in Preparation Example 2. The coating solution (2) was a colloidal solution in which the colloid of PMEA was dispersed.

Regarding the above coating solution (2), when a colloid average particle size was measured in the same manner as in Example 1-1, an average particle size of the PMEA polymer colloid was 190 nm.

Example 1-3

A coating solution (3) was obtained in the same manner as in Example 1-1 except that PMEA used in Example 1-1 was changed to PMEA (3) (weight average molecular weight=420,000) synthesized in Preparation Example 3. The coating solution (3) was a colloidal solution in which the colloid of PMEA was dispersed.

Regarding the above coating solution (3), when a colloid average particle size was measured in the same manner as in Example 1-1, an average particle size of the PMEA polymer colloid was 240 nm.

Comparative Example 1-1

PMEA (weight average molecular weight=310,000) synthesized in Preparation Example 2 was dispersed in a mixed solvent of water, methanol, and ethanol (mixing ratio (volume ratio) of water:methanol:ethanol=60:10:30) so that the concentration of PMEA becomes 0.1% by weight, and therefore a comparative coating solution (1) was prepared. The above comparative coating solution (1) was not a colloidal solution but a uniform solution.

Comparative Example 1-2

0.4 g of PMEA (4) (weight average molecular weight=800,000) synthesized in Preparation Example 4 was dissolved in 20 g of methanol. To another container, 380 g of distilled water was added, and the methanol solution of PMEA (4) above was added at a rate of 20 g/min while stirring with a stirrer. At this time, attachment of polymer aggregates was remarkable on a wall surface of the container, and it was not possible to obtain a coating solution usable for production of an artificial lung.

Table 1 below summarizes the physical properties of the coating solutions prepared in the above examples and the comparative examples. In Table 1 below, for an average particle size of the colloid particles in the colloidal solution, average particle size±standard deviation ($\mu \pm \sigma$) is described, and a coefficient of variation (CV) of a particle size of the colloid and a ratio (($\mu-\sigma$)/r) of [average particle size of colloid ($\mu$)−standard deviation ($\sigma$)] to a diameter (r) of the opening portions of the hollow fiber membranes are also described. A coefficient of variation (CV) is a value obtained by the above described formula. As a diameter (r) of the opening portions of the hollow fiber membranes, an average diameter (80 nm) of the opening portions of the hollow fiber membranes used in Examples 2-1 and 2-2 was used.

TABLE 1

| | Coating solution | Weight average molecular weight of PMEA (Mw) | Solvent of coating solution | Average particle size of PMEA polymer colloid ($\mu \pm \sigma$) [nm] | Coefficient of variation (CV) of particle size of colloid [%] | ($\mu - \sigma$)/r |
|---|---|---|---|---|---|---|
| Example 1-1 | Coating solution (1) | 250,000 | Water:MeOH = 95:5 | 160 ± 35 | 22 | 1.56 |
| Example 1-2 | Coating solution (2) | 310,000 | Water:MeOH = 95:5 | 190 ± 40 | 21 | 1.88 |
| Example 1-3 | Coating solution (3) | 420,000 | Water:MeOH = 95:5 | 240 ± 60 | 25 | 2.25 |
| Comparative Example 1-1 | Comparative coating solution (1) | 310,000 | Water:MeOH:EtOH = 60:10:30 | No colloid formed | — | — |

TABLE 1-continued

| Coating solution | Weight average molecular weight of PMEA (Mw) | Solvent of coating solution | Average particle size of PMEA polymer colloid (μ ± σ) [nm] | Coefficient of variation (CV) of particle size of colloid [%] | (μ − σ)/r |
|---|---|---|---|---|---|
| Comparative Example 1-2 | — (*1) | 800,000 | Water:MeOH = 95:5 | — (*1) | — (*1) | — (*1) |

(*1): it was not possible to obtain a coating solution usable for production of an artificial lung.

From the results in Table 1, it was found that when a weight average molecular weight of PMEA exceeds 200,000 and is less than 800,000, it was possible to prepare a colloidal solution in which an average particle size of the colloid particles in the colloidal solution is sufficiently large (140 nm or larger). On the other hand, when a weight average molecular weight of PMEA was 800,000, it was not possible to disperse PMEA in the solvent, and therefore it was not possible to prepare a coating solution usable for preparation of an artificial lung.

When preparing the coating solution, a colloidal solution can be prepared by appropriately selecting the solvent to be used. For example, it became clear that it is exemplary to use a solvent containing water and methanol.

<Production of Artificial Lung>

Example 2-1

About 20,000 porous hollow fiber membranes for gas exchange made of porous polypropylene having the inner diameter of 195 μm, the outer diameter of 295 μm, the wall thickness of 50 μm, the porosity of about 35% by volume, and a hole size of the outer surfaces (that is, an average diameter of the opening portions) of 80 nm were accommodated in a housing, and therefore a hollow fiber membrane artificial lung (a) of an outside blood flow type that has a membrane area of 1.8 m² and that is described in FIG. 1 of U.S. Pat. No. 6,495,101 B1 (corresponding to JP-A-11-114056 and EP 0 908 191) was produced.

The blood flow path of this artificial lung (a) was filled with the coating solution (2) prepared in Example 1-2 and allowed to stand at 25° C. for 120 seconds, and then the coating solution was removed, air of a flow volume of 80 L was allowed to flow, the hollow fiber membranes were dried, and therefore a hollow fiber membrane artificial lung (1) of an outside blood flow type having hollow fiber membranes in which a coat is formed on the outer surfaces was produced. The hollow fiber membrane artificial lung (1) of an outside blood flow type obtained as above may be referred to as the artificial lung (1).

Example 2-2

A hollow fiber membrane artificial lung (2) of an outside blood flow type was produced in the same manner as Example 2-1 except that a wall thickness of the porous hollow fiber membranes for gas exchange was set to 25 μm in Example 2-1. Note that the hollow fiber membrane artificial lung (2) of an outside blood flow type obtained as above may be referred to as the artificial lung (2).

Example 2-3

About 20,000 porous hollow fiber membranes for gas exchange made of porous polypropylene having the inner diameter of 195 μm, the outer diameter of 295 μm, the wall thickness of 25 μm, the porosity of about 35% by volume, and a hole size of the outer surface (that is, an average diameter of the opening portions) of 80 nm were accommodated in a housing, and therefore a hollow fiber membrane artificial lung (b) of an outside blood flow type that has a membrane area of 1.8 m² and that is described in FIG. 1 of U.S. Pat. No. 6,495,101 B1 (corresponding to JP-A-11-114056 and EP 0 908 191) was produced.

Using a roller pump, the coating solution (2) prepared in Example 1-2 was allowed to circulate for 5 minutes at a flow rate of 4 L/min in the blood flow path of this artificial lung (b), the coating solution was removed, air of a flow volume of 80 L was allowed to flow to dry the hollow fiber membranes, and therefore a hollow fiber membrane artificial lung (3) of an outside blood flow type having hollow fiber membranes in which a coating is formed on the outer surfaces was produced.

Specifically, a beaker injected with 300 mL of the coating solution (2) prepared in Example 1-2, and a roller pump were prepared. Next, the coating solution (2) in the beaker and the roller pump, the roller pump and the hollow fiber membrane artificial lung (b) of an outside blood flow type, and the hollow fiber membrane artificial lung (b) of an outside blood flow type and the coating solution (2) in the beaker were allowed to communicate with each other through a soft vinyl chloride tube, and a coating solution circuit containing the coating solution (2) in the beaker, the roller pump, and the hollow fiber membrane artificial lung (b) of an outside blood flow type, was filled with the coating solution (2) in a manner of not allowing air to enter. Then, the roller pump was operated and the coating solution (2) was allowed to circulate for 5 minutes at a flow rate of 4 L/min in the blood flow path of the artificial lung (b). Thereafter, the coating solution (2) was removed from the blood circuit of the artificial lung (b), air of a flow volume of 80 L was allowed to flow into the blood circuit of the artificial lung (b) to dry the hollow fiber membranes, and therefore a hollow fiber membrane artificial lung (3) of an outside blood flow type having hollow fiber membranes in which a coating is formed on the outer surfaces was produced. The hollow fiber membrane artificial lung (3) of an outside blood flow type obtained as above may be referred to as the artificial lung (3).

At this time, a degree of the transparency of the coating solution (2) in the beaker after circulation of the coating solution (2) in the blood circuit of the artificial lung (b) by operation of the roller pump was high compared to a degree of the transparency of the coating solution (2) before operation of the roller pump. Therefore, when manufacturing the artificial lung (3), it was visually confirmed that the coating was formed on the outer surfaces of the hollow fiber membranes by seeing a degree of white turbidity of the coating solution (2) in the beaker.

Comparative Example 2-1

A comparative hollow fiber membrane artificial lung (1) of an outside blood flow type was produced in the same manner as in Example 2-1 except that the coating solution used in Example 2-1 was changed to a comparative PMEA polymer solution (1) prepared in Comparative Example 1-1. The comparative hollow fiber membrane artificial lung (1) of an outside blood flow type obtained as above may be referred to as the comparative artificial lung (1).

Experiment 1. Evaluation of Blood Plasma Leakage Resistance Performance

With respect to the artificial lungs (1) to (3) of Examples 2-1 to 2-3 and the comparative artificial lung (1) of Comparative Example 2-1, the blood plasma leakage resistance performance was evaluated by the following method. The results are shown in Table 2 below.

Figure 8:
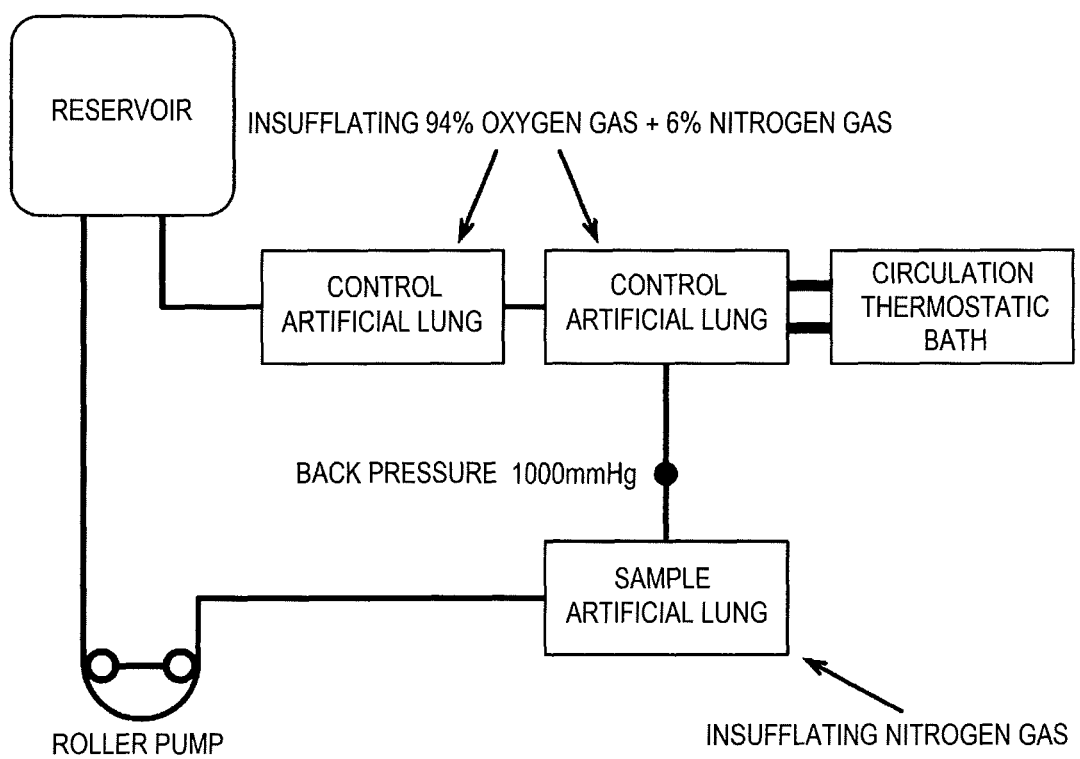
FIG. 8 is a drawing showing a test system for conducting the blood plasma leakage resistance performance test in Experiment 1, according to one aspect.

FIG. 8 is a view showing a test system of the blood plasma leakage resistance performance test. As shown in FIG. 8, this test system is composed of a reservoir, a roller pump, and the artificial lung with a built-in heat exchanger (also referred to as "a control artificial lung") which is not an evaluation sample. Among these, as the reservoir, a soft bag type is used. Note that every circuit of this test is a closed circuit that is not open to the atmosphere.

Bovine blood plasma is used as a working fluid, and the blood plasma concentrated (water removed) with a hemoconcentrator such that a surface tension becomes 43±2 dyn/cm in order to accelerate blood plasma leakage is used as a working fluid. This bovine blood plasma (working fluid) is circulated in the circuit by the roller pump and the temperature is controlled to 37±0.5° C. by a heat exchanger. Oxygen gas (94% oxygen gas and 6% nitrogen gas) is insufflated into the control artificial lung to raise the oxygen partial pressure in the bovine blood plasma, and the bovine blood plasma with a high oxygen partial pressure of about 650±50 mmHg of oxygen partial pressure is allowed to flow into the artificial lung (hereinafter also referred to as the "sample artificial lung") which is an evaluation sample. By insufflating nitrogen gas (100% nitrogen gas) into the sample artificial lung, the oxygen partial pressure of the blood plasma at the outlet of the sample artificial lung decreases as compared with that at the inlet of the sample artificial lung. The gas exchange performance can be continuously measured by a difference in this oxygen partial pressure.

The experiment was conducted for 9 hours, and the difference in the oxygen partial pressure between the start of the experiment (0 hour) and the 9th hour after the start of the experiment is evaluated as the blood plasma leakage resistance performance. The smaller the oxygen partial pressure difference becomes, the higher the blood plasma leakage resistance performance becomes. In addition, in order to accelerate the blood plasma leakage, a back pressure (outlet pressure) of the sample artificial lung is set to 1,000 mmHg.

TABLE 2

| | Artificial lung | Weight average molecular weight of PMEA (Mw) | Solvent | Colloid average particle size/hole size of surface of hollow fiber membranes | Blood plasma leakage resistance performance [mmHg] |
|---|---|---|---|---|---|
| Example 2-1 | Artificial lung (1) | 310,000 | Water:MeOH = 95:5 | 2.4 | 5.5 |
| Example 2-2 | Artificial lung (2) | 310,000 | Water:MeOH = 95:5 | 2.4 | 6.8 |
| Example 2-3 | Artificial lung (3) | 310,000 | Water:MeOH = 95:5 | 2.4 | 6.8 |
| Comparative Example 2-1 | Comparative artificial lung kay (1) | 310,000 | Water:MeOH:EtOH = 60:10:30 | — (*1) | 6.4 |

(*1): it was not possible to obtain a colloidal solution.

From the results in Table 2, it has been found that the artificial lung (1) of one aspect of the present disclosure (wall thickness=50 μm) can significantly suppress blood plasma leakage (blood plasma leakage resistance performance is significantly low) compared to the comparative artificial lung (1) (wall thickness=50 μm) in which the hollow fiber membranes were coated with colloidal solution in which a relationship between a colloid average particle size and a hole size of the surfaces of the hollow fiber membranes (average diameter of the opening portions) is out of the exemplary range of the present disclosure.

Furthermore, the artificial lung (2) according to one aspect of the present disclosure is an artificial lung of an aspect in which a wall thickness of the hollow fiber membranes is thin (wall thickness=25 μm). From the results in Table 2, it has been found that the artificial lung of one aspect of the present disclosure effectively suppresses blood plasma leakage after circulation even in the hollow fiber membranes having a thin wall thickness, to the same extent as that of Comparative Example 1 having a thick wall thickness. It is shown that in the comparative artificial lung (1) of Comparative Example 1, the blood plasma leakage resistance performance is lower (blood plasma leakage can be suppressed) than the artificial lung (2) of Example 2-2, and this can be explained as follows. That is, the comparative artificial lung (1) is thicker than the artificial lung (2) in wall thickness of the hollow fiber membranes (comparative artificial lung (1): 50 μm, artificial lung (2): 25 μm), and therefore even if blood plasma infiltrates into the holes of the hollow fiber membranes, blood plasma hardly penetrates into the lumen of the hollow fiber. Accordingly, it is considered that the blood plasma leakage resistance performance is low as a consequence (blood plasma leakage can be suppressed).

Furthermore, since the blood plasma leakage resistance performances in the artificial lung (2) and the artificial lung (3) are the same as each other, the colloidal solution of the antithrombotic material used in the artificial lung according to one aspect of the present disclosure can significantly suppress blood plasma leakage without depending on the coating method thereof.

The detailed description above describes exemplary embodiments of an artificial lung and exemplary embodiments of a method for manufacturing an artificial lung. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An artificial lung, comprising:
   a plurality of porous hollow fiber membranes for gas exchange,
   wherein the hollow fiber membranes have outer surfaces, inner surfaces forming lumens, and opening portions through which the outer surfaces communicate with the inner surfaces,
   wherein any one of the outer surfaces and the inner surfaces is coated with a colloidal solution of an antithrombotic material containing a polymer as a main component, and
   wherein an average particle size of colloid particles in the colloidal solution is at least 1.5 times an average diameter of the opening portions of the hollow fiber membranes.

2. The artificial lung according to claim 1,
   wherein the hollow fiber membranes are for accommodating a flow of an oxygen-containing gas inside the lumens, and the outer surfaces of the hollow fiber membranes are for contacting blood, and
   the outer surfaces are coated with the colloidal solution.

3. The artificial lung according to claim 1,
   wherein the hollow fiber membranes are for accommodating blood inside the lumens, and the outer surfaces of the hollow fiber membranes are for contacting a flow of an oxygen-containing gas, and
   the inner surfaces are coated with the colloidal solution.

4. The artificial lung according to claim 1,
   wherein the average particle size of the colloid particles in the colloidal solution is 140 nm or larger.

5. The artificial lung according to claim 4, wherein the average particle size of the colloid particles in the colloidal solution is in a range of 140 nm to 400 nm.

6. The artificial lung according to claim 1,
   wherein the polymer has a structural unit derived from alkoxyalkyl (meth)acrylate represented by Formula (I):

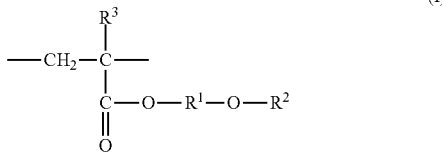

wherein in Formula (I), $R^3$ represents a hydrogen atom or a methyl group, $R^1$ represents an alkylene group having 1 to 4 carbon atoms, and $R^2$ represents an alkyl group having 1 to 4 carbon atoms.

7. The artificial lung according to claim 1,
   wherein a weight average molecular weight of the polymer is more than 200,000 and less than 800,000.

8. The artificial lung according to claim 1,
   wherein a solvent of the colloidal solution contains water and methanol in a mixing ratio of 6:1 to 32:1, based on the volume of the water and methanol.

9. The artificial lung according to claim 1,
   wherein a blood plasma leakage resistance performance of the artifical lung is 15 mmHg or less.

10. The artificial lung according to claim 1, wherein a ratio of the average particle size of colloid particles in the colloidal solution to the average diameter of the opening portions of the hollow fiber membranes is 1.5:1 to 5.0:1.

11. A method for manufacturing an artificial lung having a plurality of porous hollow fiber membranes for gas exchange which have outer surfaces, inner surfaces forming lumens, and opening portions through which the outer surfaces communicate with the inner surfaces, the method comprising:
    preparing a colloidal solution of an antithrombotic material containing a polymer as a main component, and
    coating any one of the outer surfaces and the inner surfaces of the hollow fiber membranes with a colloidal solution of an antithrombotic material containing a polymer as a main component,
    wherein an average particle size of colloid particles in the colloidal solution is at least 1.5 times an average diameter of the opening portions of the hollow fiber membranes.

12. The method for manufacturing an artificial lung according to claim 11,
    wherein the hollow fiber membranes are for accommodating a flow of an oxygen-containing gas inside the lumens, and the outer surfaces of the hollow fiber membranes are for contacting blood, and
    the outer surfaces are coated with the colloidal solution.

13. The method for manufacturing an artificial lung according to claim 11,
    wherein the hollow fiber membranes are for accommodating blood inside the lumens, and the outer surfaces of the hollow fiber membranes are for contacting a flow of an oxygen-containing gas, and
    the inner surfaces are coated with the colloidal solution.

14. The method for manufacturing an artificial lung according to claim 11,
    wherein an average particle size of the colloid particles in the colloidal solution is 140 nm or larger.

15. The method for manufacturing an artificial lung according to claim 14, wherein the average particle size of the colloid particles in the colloidal solution is in a range of 140 nm to 400 nm.

16. The method for manufacturing an artificial lung according to claim 11,
    wherein the polymer has a structural unit derived from alkoxyalkyl (meth)acrylate represented by Formula (I)

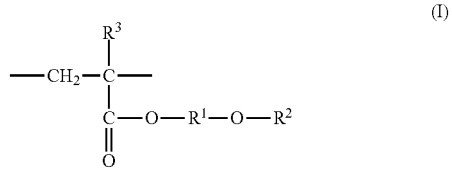

wherein in Formula (I), $R^3$ represents a hydrogen atom or a methyl group, $R^1$ represents an alkylene group having 1 to 4 carbon atoms, and $R^2$ represents an alkyl group having 1 to 4 carbon atoms.

17. The method for manufacturing an artificial lung according to claim 11,
    wherein a weight average molecular weight of the polymer is more than 200,000 and less than 800,000.

18. The method for manufacturing an artificial lung according to claim 11, wherein a solvent of the colloidal solution contains water and methanol in a mixing ratio of 6:1 to 32:1, based on the volume of the water and methanol.

19. The method for manufacturing an artificial lung according to claim 11,
wherein the colloidal solution satisfies at least one of the following (a) and (b):
(a) a coefficient of variation (CV) of a particle size of a colloid is 30% or less, and (b) average particle size of colloid ($\mu$)−standard deviation ($\sigma$)≥1.05×diameter of opening portions of hollow fiber membranes.

20. The method for manufacturing an artificial lung according to claim 11,
wherein a blood plasma leakage resistance performance of the artifical lung is 15 mmHg or less.

21. The method for manufacturing an artificial lung according to claim 11, wherein a ratio of the average particle size of colloid particles in the colloidal solution to the average diameter of the opening portions of the hollow fiber membranes is 1.5:1 to 5.0:1.

22. A method for manufacturing an artificial lung having a plurality of porous hollow fiber membranes for gas exchange which have outer surfaces, inner surfaces forming lumens, and opening portions through which the outer surfaces communicate with the inner surfaces, the method comprising:
coating any one of the outer surfaces and the inner surfaces of the hollow fiber membranes with a colloidal solution of an antithrombotic material containing a polymer as a main component,
wherein an average particle size of colloid particles in the colloidal solution is at least 1.5 times an average diameter of the opening portions of the hollow fiber membranes.

23. The method for manufacturing an artificial lung according to claim 22,
wherein the average particle size of the colloid particles in the colloidal solution is 140 nm or larger.

24. The method for manufacturing an artificial lung according to claim 23, wherein the average particle size of the colloid particles in the colloidal solution is in a range of 140 nm to 400 nm.

25. The method for manufacturing an artificial lung according to claim 22,
wherein a weight average molecular weight of the polymer is more than 200,000 and less than 800,000.

26. The method for manufacturing an artificial lung according to claim 22, wherein a ratio of the average particle size of colloid particles in the colloidal solution to the average diameter of the opening portions of the hollow fiber membranes is 1.5:1 to 5.0:1.

* * * * *